US010300167B2

(12) United States Patent
McGowan et al.

(10) Patent No.: US 10,300,167 B2
(45) Date of Patent: May 28, 2019

(54) FUNCTIONALIZED CALCIUM PHOSPHATE ARTIFICIAL BONE AND JOINT COMPOSITIONS AND METHODS OF USE AND MANUFACTURE

(75) Inventors: Kenneth A. McGowan, Harrison City, PA (US); Ellen S. Gawalt, Pittsburgh, PA (US); Rachelle Palchesko, Lucerenmines, PA (US)

(73) Assignees: CAberTech, Inc., Harrison City, PA (US); Duquesne University of the Holy Spirit, Pittsburgh, PA (US)

( * ) Notice: Subject to any disclaimer, the term of this patent is extended or adjusted under 35 U.S.C. 154(b) by 0 days.

(21) Appl. No.: 13/193,231

(22) Filed: Jul. 28, 2011

(65) Prior Publication Data
US 2012/0087950 A1 Apr. 12, 2012

Related U.S. Application Data

(63) Continuation-in-part of application No. 11/728,250, filed on Mar. 23, 2007.
(Continued)

(51) Int. Cl.
*A61K 33/06* (2006.01)
*C12N 5/00* (2006.01)
(Continued)

(52) U.S. Cl.
CPC ............... *A61L 27/10* (2013.01); *A61L 27/12* (2013.01); *A61L 27/54* (2013.01); *C12N 5/0654* (2013.01);
(Continued)

(58) Field of Classification Search
None
See application file for complete search history.

(56) References Cited

U.S. PATENT DOCUMENTS 3,312,558 A 4/1967 Miller
4,218,255 A 8/1980 Bajpai et al.
(Continued)

FOREIGN PATENT DOCUMENTS

WO 2004072104 8/2004
WO 2005032417 4/2005
(Continued)

OTHER PUBLICATIONS

Geiger, G., Bone Cement, Technology Briefs, American Ceramic Society Bulletin, 2003, 5, vol. 82, No. 11, American Cancer Society.
(Continued)

*Primary Examiner* — Jianfeng Song
(74) *Attorney, Agent, or Firm* — Buchanan Ingersoll & Rooney PC; Craig G. Cochenour, Esq.

(57) ABSTRACT

The present invention provides a functionalized composition and resulting functionalized body or prosthesis for in vitro and in vivo use comprising at least one calcium phosphate containing phase that is functionalized with a linker group comprising at least one of an organic acid molecule, a phosphonic acid, an amine, N,N-dicyclohexylcarbodiimide, and 3-maleimidopropionic acid N-hydroxysuccinimide ester, and combinations thereof, and one or more of a chemical and/or a biologically active moieties, wherein the linker group provides for a reactive location for the attachment of the chemical or biologically active moiety, or both, to the calcium phosphate containing phase, and optionally including an unmodified and/or modified calcium aluminate containing phase. Methods of manufacturing a functionalized artificial prosthesis and methods of repairing a bone, vertebrae, or tissue structures are provided.

12 Claims, 26 Drawing Sheets

Related U.S. Application Data

(60) Provisional application No. 60/785,477, filed on Mar. 24, 2006.

(51) Int. Cl.

| | | |
|---|---|---|
| *A61K 38/02* | (2006.01) | |
| *B29C 33/38* | (2006.01) | |
| *A61K 31/43* | (2006.01) | |
| *A61K 31/7036* | (2006.01) | |
| *A61K 38/07* | (2006.01) | |
| *A61P 19/08* | (2006.01) | |
| *A61K 9/00* | (2006.01) | |
| *A61K 38/18* | (2006.01) | |
| *A61L 27/10* | (2006.01) | |
| *A61L 27/12* | (2006.01) | |
| *A61L 27/54* | (2006.01) | |
| *C12N 5/077* | (2010.01) | |
| *A61F 2/28* | (2006.01) | |
| *A61F 2/30* | (2006.01) | |

(52) U.S. Cl.
CPC ............. *A61F 2/28* (2013.01); *A61F 2/30942* (2013.01); *A61F 2002/30677* (2013.01); *A61F 2002/30957* (2013.01); *A61F 2310/00179* (2013.01); *A61L 2300/406* (2013.01); *A61L 2300/414* (2013.01); *C12N 2501/155* (2013.01); *C12N 2533/18* (2013.01); *C12N 2533/54* (2013.01)

(56) References Cited

U.S. PATENT DOCUMENTS

| | | | |
|---|---|---|---|
| 4,755,228 A | 7/1988 | Sakurai et al. | |
| 4,908,030 A * | 3/1990 | Linkow .............. | A61F 2/30767 204/192.11 |
| 4,960,737 A | 10/1990 | Guile et al. | |
| 5,241,094 A | 8/1993 | Razvan et al. | |
| 6,689,707 B1 | 2/2004 | Beall et al. | |
| 6,713,420 B2 | 3/2004 | Imura et al. | |
| 6,723,334 B1 | 4/2004 | McGee et al. | |
| 6,809,051 B2 | 10/2004 | Beall et al. | |
| 7,025,824 B2 | 4/2006 | Axen et al. | |
| 2001/0021389 A1* | 9/2001 | Starling et al. ............... 424/422 | |
| 2002/0076528 A1 | 6/2002 | Tomsia et al. | |
| 2003/0215484 A1* | 11/2003 | Axen et al. .................. 424/423 | |
| 2004/0030408 A1 | 2/2004 | Griffin et al. | |
| 2004/0117030 A1 | 6/2004 | Axen et al. | |
| 2004/0265571 A1* | 12/2004 | Schwartz et al. ............. 428/333 | |
| 2005/0027033 A1 | 2/2005 | Knaack et al. | |
| 2005/0049717 A1* | 3/2005 | McGowan ................. 623/23.56 | |
| 2006/0194008 A1* | 8/2006 | Schwartz et al. ............. 428/34.4 | |
| 2007/0224678 A1 | 9/2007 | McGowan et al. | |
| 2009/0130173 A1 | 5/2009 | Behnam et al. | |
| 2009/0220605 A1 | 9/2009 | Wei et al. | |
| 2010/0074876 A1 | 3/2010 | Li et al. | |
| 2010/0106233 A1 | 4/2010 | Grant et al. | |
| 2010/0196478 A1 | 8/2010 | Masters | |
| 2011/0038938 A1 | 2/2011 | Ison et al. | |
| 2011/0045048 A1 | 2/2011 | Park et al. | |

FOREIGN PATENT DOCUMENTS

| | | | |
|---|---|---|---|
| WO | 2005089826 | | 9/2005 |
| WO | 2010021601 A1 | | 2/2010 |
| WO | WO-2010021601 | * | 2/2010 |

OTHER PUBLICATIONS

Kalita, S. J. et al., Porous Calcium Aluminate Ceramics for Bone-Graft Applications, Abstract, Journal of Materials Research, 2002, vol. 17 No. 12, Materials Research Society.

Kopanda, J.E. et al., Production Processes, Properties, and Applications for Calcium Aluminate Cements, Science and Technology Handbook, 1990, 171-183, Am. Ceram. Sci.

Graves, et al., Resorbable Ceramic Implants, J. Biomed. Mat. Research Symposium, 1971, 91-115, No. 2 (Part 1).

McGowan, K.A. et al., PCT/US2012/046444, Search Report and Written Opinion, dated Dec. 7, 2012.

Sternberger, L.A., et al., A General Method for the Specific Purification of Antiprotein Antibodies, The Sloan-Kettering Institute for Cancer Research, 1950, 65-73, New York, NY.

Fischer, H., et al., Bioactivation of Inert Alumina Ceramics by Hydroxylation, J. Biomaterials, 2005, 6151-6157, vol. 26, Sciencedirect.com, Elsevier Ltd.

Extended European Search Report for EP Application No. 07753796.7, dated May 3, 2016.

* cited by examiner

Day 1      Day 4      Day 7

|  | Day 1 | Day 4 | Day 7 |
|---|---|---|---|
| Static Culture | 90±3% | 95±2% | 94±2% |
| Dynamic Culture | 91±2% | 93±2% | 94±2% |

Independent experiments (n=2)

Independent experiments (n=5)

| Treatment | Alkaline Phosphatase Activity (pmol product / microg protein / 60 min) |
|---|---|
| Control medium | 84 ± 13 |
| OS+ medium | 235 ± 47 |

All spectra shown are after deposition and subsequent rinsing and sonication

Phosphonic Acid

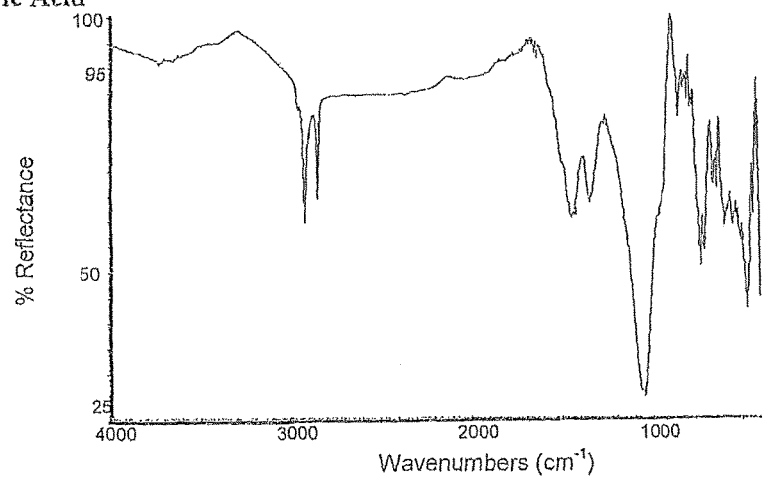

Fig 8. Octadecylphosphonic acid P-O 1047, P=O 1346 no P-O-H therefore covalently bound; C-H region shows ordered alkyl chains Carboxylic Acids (examples)

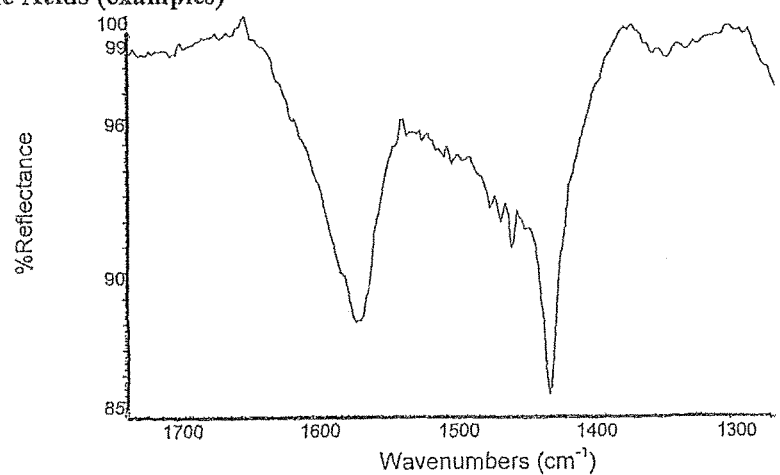

Fig 9. C-O region of 16-hydroxyhexadecanoic acid Peak at 1568 for C-O, absence of C=O at 1700 indicating binding to the surface through C-O bidentate mode binding

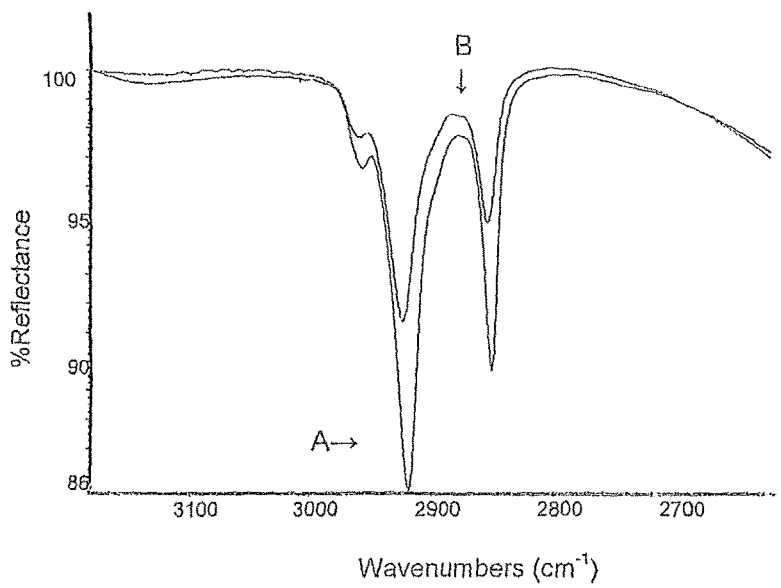
Fig 10. Stearic acid on calcium aluminate
Deposited-blue "A" peaks: 2956  2918  2850
Rinsed- Red "B" peaks: 2958  2923  2852
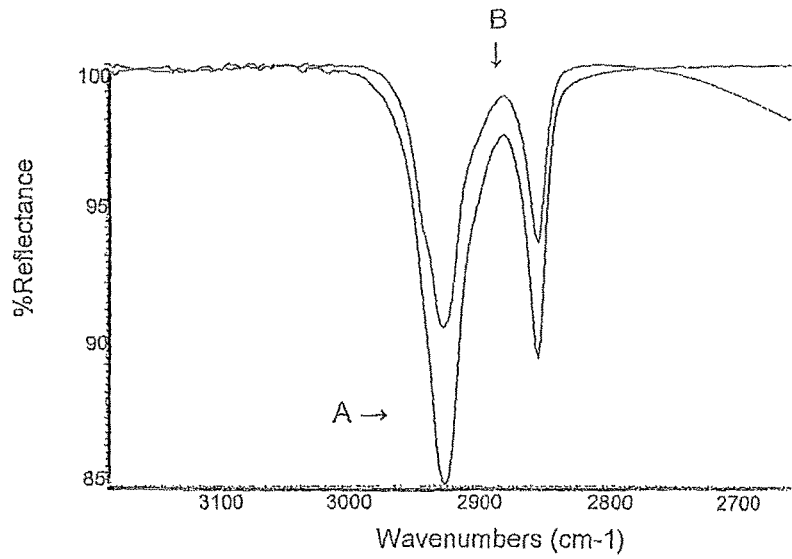
Fig 11. 1,12-dodecanedicarboxylic acid on calcium aluminate
Deposited-blue "A" peaks: 2921  2850
Rinsed- Red "B" peaks: 2923  2850

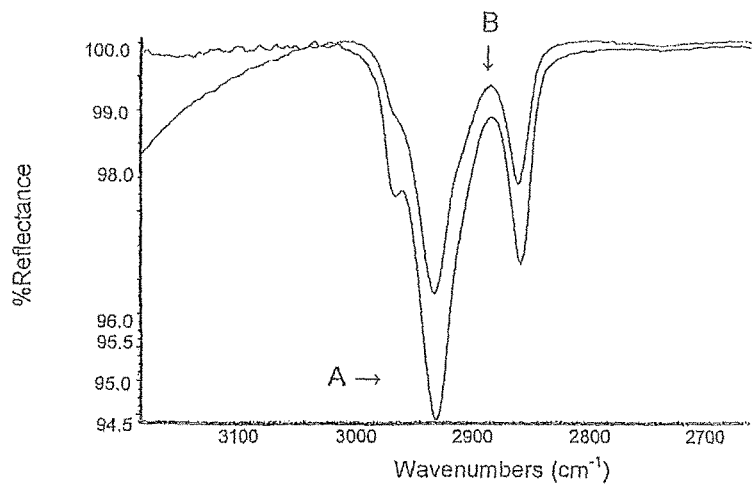
Fig 12.  12-aminododecanoic acid on calcium aluminate
Deposited-blue "A" peaks:  2962  2926  2854
Rinsed- Red "B" peaks:  -----  2927  2856
Amines
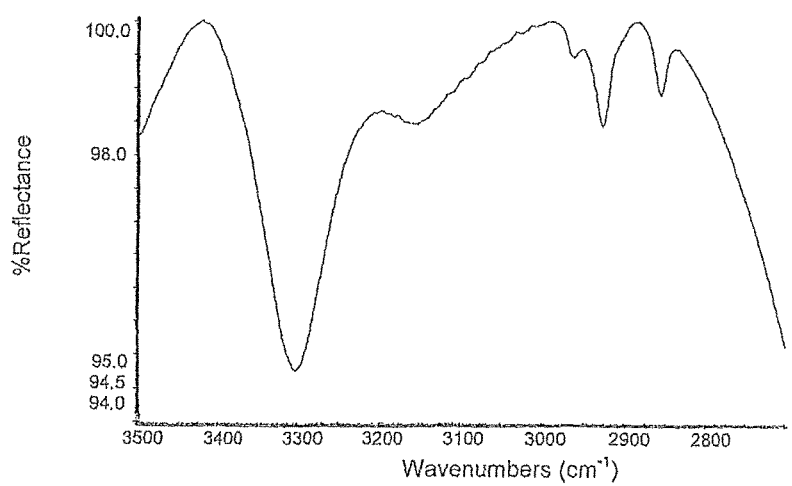
Fig 13.  Octadecylamine _peaks attributed to C-H stretch of $CH_2$ and $CH_3$ are seen, as well as N-H stretching of $NH_2$ at 3322 $cm^{-1}$ Coupling chemistry
Ampicillin attached by DCC coupling via 1,12 dodecanedicarboxylic acid
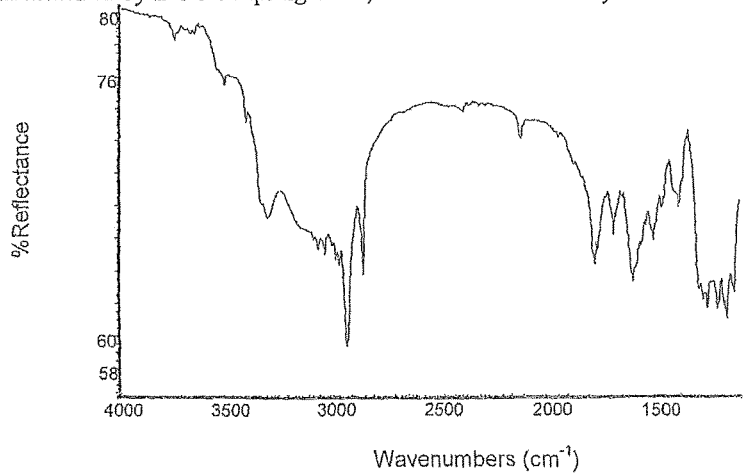
Fig 14. Peaks for ampicillin can be seen at 3401, 3332, 3029 cm. Overlay with ampicillin below. Linker of 1,12 dicarboxylic is seen by the large C-H stretching peaks still seen in IR.
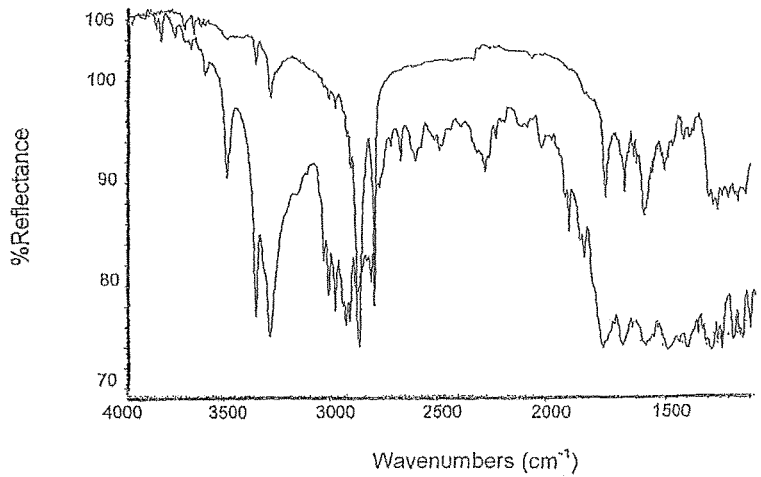
Fig 15. Ampicillin powder (lower spectra) overlayed with ampicillin attached to CA via linkers RGDC attached via maleimide coupling to 12-aminododecanoic acid on calcium aluminate Chemistry

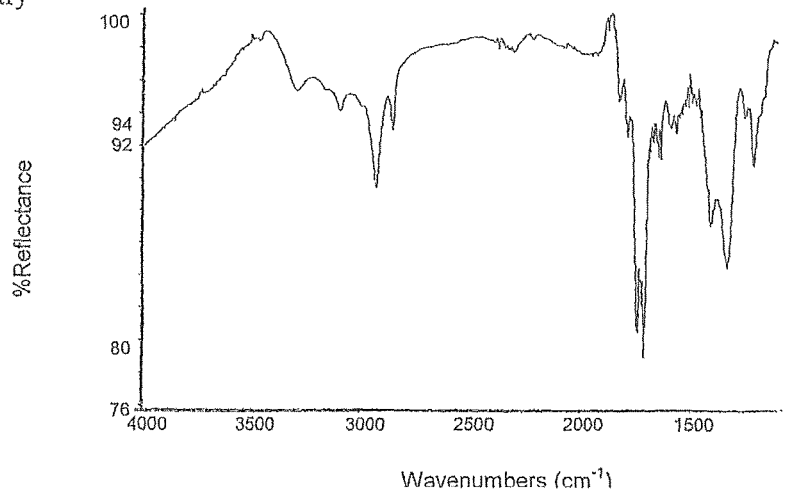

Fig 16. 3-maleimidopropionic acid .N-Hydroxysuccinimide ester attached to 12-aminododecanoic acid. Peaks in the 1700 region are consistent with maleimide deposition, cyclic imide C=O peak at 1738.

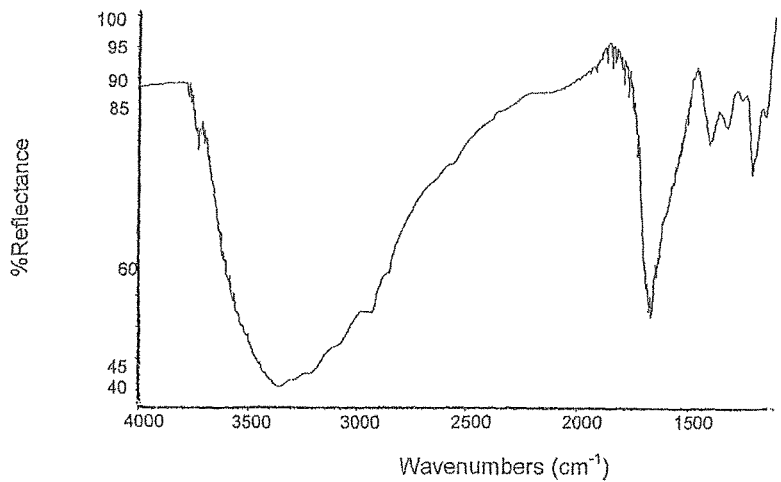

Fig. 17. RGDC attached via maleimide coupling. Peak at 1733 consistent with C=O from maleimide, while the peak at 1665 is consistent with the amide I stretch and the presence of the peptides on the surface.

FIG. 18

Bone Implants

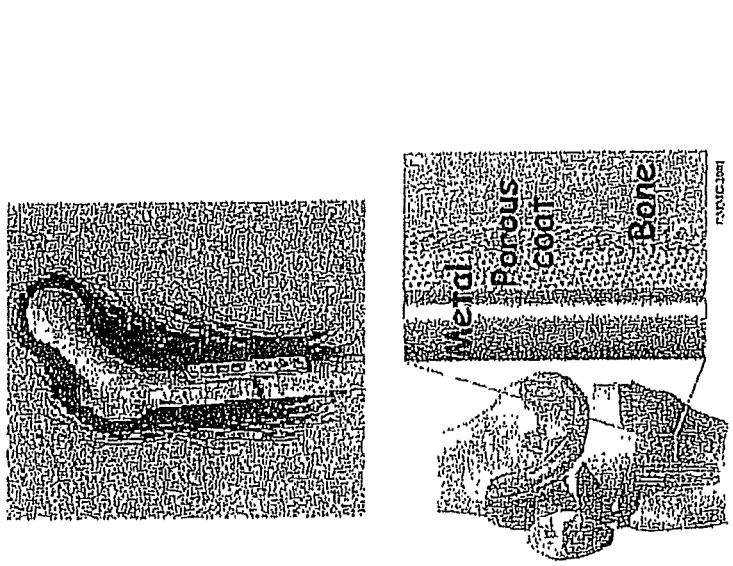

- Bone implants are used to help repair or to replace damaged bone tissue
- In order to work, bone implant material, must be mechanically strong, capable of bonding to the bone (osteoconductive)
- One common problem with bone implant surgeries is that infections often occur at the site of the implant
- It would be advantageous to develop new bone implant materials that resist infections

FIG. 19

Calcium Aluminate

☐ Properties of calcium aluminate compositions are suitable bone implant material
  - Mechanically Strong
  - Castable
  - Porous (facilitates bone cell attachment)

☐ We are trying to improve the compatibility between the implant and surrounding tissues by forming a functionalized interface between the calcium aluminate compositions surface and the biological tissue in order to improve the material's biocompatibility and resistance to infection

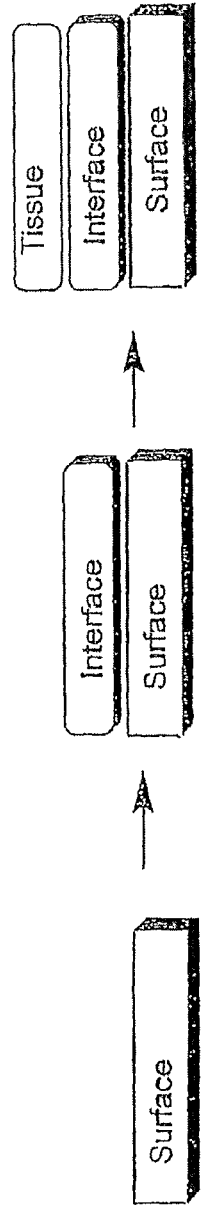

Chemical Surface Modification

☐ Surfaces are functionalized with long-chain organic acids.
☐ Head group of acid molecules bind to the metal oxide surface of the ceramic

Phosphonic acid binding

- Spectrum shows octadecylphosphonic acid
- Presence of hydrocarbon peaks on CA surface indicates that molecules adsorbed onto the surface
- Phosphonic acid molecules did not desorb during rinse or sonication tests Phosphonic s2

Coupling Chemistry

- Above scheme shows method for bonding ampicillin, a common antibiotic agent, to the surface using N,N-dicyclohexylcarbodiimide (DCC) as a coupling agent
- Using coupling agents, larger molecules can be attached to the functionalized surface FIG. 26 RGDC Peptide coupling modification of calcium aluminate material Reaction between ceramic and organic, where M= Al or Ca and X is the variable tail group The following shows the infrared spectra of the C-H region of a calcium aluminate material of the present invention functionalized with octadecylcarboxylic acid.

Schematic representation of BMP-2 attachment to CA

FUNCTIONALIZED CALCIUM PHOSPHATE ARTIFICIAL BONE AND JOINT COMPOSITIONS AND METHODS OF USE AND MANUFACTURE

CROSS-REFERENCE TO RELATED APPLICATION

This application is a continuation-in-part application of U.S. patent application Ser. No. 11/728,250 filed Mar. 23, 2007, entitled "Functionalized Artificial Bone and Joint Compositions and Methods of Use and Manufacture", based on U.S. Provisional Application Ser. No. 60/785,477, and claims the benefit of priority thereto. The text of U.S. patent application Ser. No. 11/728,250 is incorporated by reference into this application as if fully rewritten herein.

BACKGROUND OF THE INVENTION

1. Field of the Invention

The use of calcium phosphate and optionally a calcium aluminate (all associated phases, derivatives, and/or analogs thereof) as raw materials for the manufacture of artificial bone, artificial joints, in-vitro support structures, and support structure for tissue, cells, and/or organ growth and/or regeneration is provided. The use of slipcasting, slurrycasting or vibration casting in molds to generate the desired shapes of the artificial bones, joints and support structures of the invention, as well as generating the desired shapes by hand without a mold, are also provided. The present invention provides a functionalized composition comprising at least one calcium phosphate containing phase that is functionalized either on the surface of the calcium phosphate containing phase or within a porous scaffold of the calcium phosphate containing phase with a linker group comprising at least one of an organic acid molecule, a phosphonic acid, an amine, N,N-dicyclohexylcarbodiimide, and 3-maleimidopropionic acid N-hydroxysuccinimide ester, and combinations thereof, and one or more of another chemical moiety and/or one or more of a biologically active moiety, wherein the linker group provides for a reactive location for the attachment of either of the another chemical moiety or the biologically active moiety, or both, to the calcium phosphate containing phase, and optionally including wherein at least one of the calcium phosphate containing phases is in a monolithic form. Further, a functionalized composition is provided having the calcium phosphate containing phase as described above and optionally a calcium aluminate containing phase that optionally is functionalized with one or a plurality of the above-mentioned linker groups for providing a reactive location for the attachment of other chemical and/or biologically active moieties to the calcium aluminate containing phase.

2. Description of the Background Art

Current artificial joints and bones are manufactured from apatites or metal, typically titanium. They are machined to the desired shape which is a costly and production inefficient method of construction. These materials, in order to be accommodated by the host, must exhibit porosity so as to accommodate cell growth within the three dimensional structure. In particular, porosity is important where the part comes in contact with the host's natural structure (bone). This is due to the need for the host's bone to grow into and vascularize the artificial structure in order to develop the necessary bond between the two and reduce bone degeneration at the interface. Although attempts have been made in the current materials known by those skilled in the art to introduce porosity, the resulting structure is less than ideal. In most cases, artificial joints and other structures need to be replaced over time because the surrounding tissue and structure has degenerated. Pins, screws, rods and other structures are required to stabilize, bond and support the interface.

There is an identifiable need to create structures designed to support tissue growth, such as in artificial organ growth. The use of plastics as a support structure for tissue growth is known by those skilled in the art and has been accomplished by the use of organic polymers. These plastics and polymers are expensive when employed as artificial prostheses and lack porosity.

Bone is a very complex organ made of cells and extracellular matrix. It is constantly being rebuilt through the interactions of osteoblasts and osteoclasts. Bone functions include maintaining blood calcium levels, providing mechanical support to soft tissues, and serving as levers for muscle action, supporting haematopoiesis, and housing the brain and spinal cord.

The treatment of bone diseases and fractures represents one of the largest markets for regenerative medicine, estimated to reach $1.8 billion by 2008. Annually, there are over 500,000 bone graft procedures in the United States. Of these procedures, only 10% involve synthetic sources.

Bone fracture and damage result in more than 1.3 million surgical procedures each year only in the United States. Autografts and allografts are considered the standard for treating these types of wounds. However, both methods have disadvantages. The failure rate of an autograft is controlled by the need of a second site of surgery. The necessity of a second site of surgery for donor material contributes to the failure rate of autograft procedures. Failure can be attributed to limited supply, inadequate size and shape, and the morbidity associated with the donor site; all of which are issues of concern. Allografts share some of these disadvantages, and in addition; the procedure raises questions associated with donor and recipient compatibility. The disadvantages of autografts and allografts have influenced the importance of synthetic bone implants. The calcium aluminate materials of the present invention are effective bone replacement material. It will be appreciated by those skilled in the art that the calcium aluminate materials of the present invention have a controlled porosity, high strength and ease of casting, and overcome many of the difficulties associated with currently available technology.

Current implant technologies involve the use of titanium and other metals which is costly due to the need to machine the material to the desired shape. These materials, in order to be accommodated by the host, must exhibit porosity where the implant comes in contact with the host's bone. This is due to the need for the host's bone to grow into and vascularize the artificial structure in order to develop the necessary bone between the two, and reduce bone degeneration at the interface. In addition, there is bone loss due to the hardness differential between the implanted metal and natural bone. Plastics are often inserted between the two to stop this from occurring but this affects the ability of the appropriate interface to form. Metal implants require the use of rods, pins, and screws to be held into place and often need to be replaced over time.

As stated herein, methods to heal damaged bone include autografts, allografts, and the use of synthetic sources. Autografts are the standard for repairing skeletal defects, however, there are disadvantages associated with this type of treatment. Reasons for failed autografts include the need for a second site of surgery, limited supply, inadequate graft size and shape, and morbidity associated with the donor site. Allografts present similar disadvantages and are further complicated by issues related to the potential of pathogenic transmission.

Synthetic sources and bone substitutes are being evaluated to overcome the difficulties involved with autografts and allografts. To be effective in healing bone defects a material needs to have certain qualities. A scaffold should be porous to allow nutrients to permeate, and permit vascularization. It should be osteoconductive to enable new bone tissue formation, and it should degrade to allow resorbtion. Demineralized bone matrix, hydroxyapatite and tricalcium phosphate granules and scaffolds, organic sponges, synthetic sponges, porous ceramics, and collagen discs have all been used as bone substitutes or vehicles to deliver bone cells or growth factors.

Current artificial joints and bones are manufactured from apatites or metal, typically titanium. They are machined to the desired shape which is a costly and production inefficient method of construction. These types of materials are not all optimized for porosity, which is crucial for a successful implant material. There is a need for the host's bone to grow into and vascularize the artificial structure in order to develop the necessary bond between the artificial and natural bone matrix. This will result in reduced bone degeneration at the interface of the implant material and natural bone.

Research to date has mainly focused on calcium aluminates for use in the dental industry as a direct restorative dental material wherein the calcium aluminate cement is used as a fine bonding agent in the matrix and is not the primary support aggregate.

Calcium aluminates do not cause an inflammatory response when placed into in-vivo scenarios. Klawitter and Hulbert studied the influence of pore structures on calcium aluminate pellets. Calcium aluminates were implanted into the midshaft region of dog femurs and showed no inflammatory response. The Klawitter and Hulbert study showed that tissue around the porous implants healed more quickly.

Other studies have shown that calcium aluminates are able to support the proliferation of cells. Kalita studied the porosity of calcium aluminates and determined that some of the pores of the calcium aluminates were almost filled with a monolayer of cells. Kalita used fused deposition process to build materials using a computer program which constructs the material layer by layer.

In spite of this background art, there remains a very real and substantial need for porous bodies comprising calcium phosphate and optionally calcium aluminate, its phases, derivatives and/or analogs thereof, wherein the porous bodies are capable of functioning as artificial bone, artificial joints, in-vitro support structures, and in-vivo support structures for cells, tissues, organs and nerve growth and regeneration.

SUMMARY OF THE INVENTION

The present invention has met the above-described need. The present invention provides a functionalized body and functionalized compositions comprising at least one calcium phosphate containing phase that is functionalized either on the surface of the calcium phosphate containing phase or within a porous scaffold of the calcium phosphate containing phase with a linker group comprising at least one of an organic acid molecule, a phosphonic acid, an amine, N,N-dicyclohexylcarbodiimide, and 3-maleimidopropionic acid N-hydroxysuccinimide ester, and combinations thereof, and one or more of another chemical moiety and/or one or more of a biologically active moiety, wherein the linker group provides for a reactive location for the attachment of either of the another chemical moiety or the biologically active moiety, or both, to the calcium phosphate containing phase, and optionally including wherein at least one of the calcium phosphate containing phases is/are in a monolithic form. The functionalized compositions of the present invention have the characteristic of a plastic consistency (as defined herein) such that the functionalized compositions are pliable by or under the force of the human hand for forming any desired three dimensional shape or structure or may be adhered to an existing three dimensional structure. These plastic functionalized compositions harden (set) over a time period within one hour or longer at ambient (room) temperatures to form a hard monolithic structure.

The calcium phosphate containing compositions of this invention may be used in the manufacture of artificial prostheses that may function as artificial bones and joints of a patient, as well as in-vitro support structures, in-vivo support structures for cells, tissues, organ and nerve growth and/or regeneration.

The present invention further provides the functionalized composition comprising the calcium phosphate containing phase that is functionalized as provided herein, wherein the functionalized composition further comprises at least one calcium aluminate phase wherein the calcium aluminate containing phase comprising one or more phases, analogs and derivatives of calcium aluminate that result from the interaction of $C_nA_y$, $C_nA_y$-hydrates, CaO, $Al_2O_3$, $Al_nO_y$-hydrates with or without $P_nO_y^x$ to form CX and/or AX and/or CAX, wherein n is an integer from about 1 to about 12, y is an integer from about 1 to about 24, x is an integer from about 1 to about 12, X is a phosphate moiety, C is CaO, and A is $Al_2O_3$. Optionally, one or more of the calcium phosphate containing phases and/or one or more of the calcium aluminate containing phases is/are in the form of a monolith. The monolith may be in the shape or size as desired, such as in the shape and size of a morsel as described herein. Optionally, the functionalized compositions of the present invention comprise at least one of a fiber, an accelerator, a retarder, a surfactant, a foaming agent, one or more reactive aluminas, and combinations thereof.

In another embodiment, the functionalized compositions as described herein further comprise wherein at least one or more of the calcium aluminate containing phases is or are functionalized either on the surface of the calcium aluminate containing phase or within a porous scaffold of the calcium aluminate containing phase with a linker group comprising at least one of an organic acid molecule, a phosphonic acid, an amine, N,N-dicyclohexylcarbodiimide, and 3-maleimidopropionic acid N-hydroxysuccinimide ester, and combinations thereof, and one or more of another chemical moiety and/or one or more of a biologically active moiety, wherein the linker group provides for a reactive location for the attachment of either of the another chemical moiety or the biologically active moiety, or both, to the calcium aluminate containing phase.

The present invention provides an artificial prosthesis for in vitro and in vivo use comprising the functionalized compositions of the present invention as described herein.

In a more preferred embodiment, the functionalized compositions of the present invention includes wherein the biologically active moiety is selected from the group consisting of a protein, an antibiotic, and a peptide, and combinations thereof, any one or more of which may be attached to the functionalized calcium phosphate containing phase and optionally attached to the functionalized calcium aluminate containing phase.

A more preferred embodiment of this invention provides wherein the calcium phosphate containing phase, and optionally the calcium aluminate containing phase, as described herein, is functionalized with an organic acid and subsequently reacted with 3-maleimidopropionic acid N-hydroxysuccinimide ester (NHS) for binding one or more proteins, antibiotics, or peptides, or combinations thereof, to an amino-functionalized calcium phosphate and optionally an amino-functionalized calcium aluminate containing phase.

The functionalized body may be an artificial prosthesis wherein the artificial prosthesis is selected from the group consisting of an artificial bone, artificial joint, in-vitro support structure, an in-vivo support structure, and a scaffolding matrix for support of cell, tissue, organ, and nerve growth.

A preferred embodiment of this invention provides wherein the functionalized composition as described herein includes wherein the organic acid has a formula of $(CO_2H)_a$ $C_nH_{2n+(-2\ through\ +2)}X_d$ wherein X is selected from the group of $CH_3$, COOH, OH, $NH_2$ and Br and wherein a is a number from about 1 to about 3, wherein n is a number from about 1 to about 1000, and wherein d is a number from about 1 to about 3.

In a more preferred embodiment of this invention, the functionalized composition as described herein includes wherein an antibiotic is the biologically active moiety attached to at least one of the calcium phosphate containing phases and optionally to at least one of the optional calcium aluminate containing phases. The antibiotic may be any antibiotic, such as for example but not limited to ampicillin, vancomycin, amoxicillin, penicillin, and gentamycin, and combinations thereof.

In a more preferred embodiment of this invention, the functionalized composition as described herein comprises a calcium phosphate containing phase that is functionalized with an organic acid and subsequently reacted with 3-maleimidopropionic acid N-hydroxysuccinimide ester (NHS). This is useful, for example but not limited to, for the binding one or more peptides to the amino-functionalized calcium phosphate containing phase.

This invention also provides for a method of making an artificial prosthesis comprising the steps of mapping of a patient's identified bone, vertebrae, or tissue structure; creating a three dimensional pattern of the identified bone, vertebrae, or tissue structure from the mapped bone, vertebrae, or tissue structure; and either (1) creating a mold or negative of the identified bone, vertebrae, or tissue structure from said pattern; and casting a functionalized composition into said mold thereby forming said artificial prosthesis, or (2) forming a three dimensional structure by hand from said pattern employing a functionalized composition thereby forming said artificial prosthesis, wherein said functionalized composition comprises a calcium phosphate containing phase (as described herein) that is functionalized with a linker group comprising at least one of an organic acid molecule, a phosphonic acid, an amine, and N,N-dicyclohexylcarbodiimide, and at least one or more of another chemical moiety (molecule or compound) or at least one or more of a biologically active moiety, wherein the linker group provides for a reactive location for the attachment of the another chemical moiety, or the biologically active moiety, or both, to the calcium phosphate containing phase. In a preferred embodiment, the method as described herein includes wherein an antibiotic, protein, or peptide, or combinations thereof, is/are the moiety(ies) attached to the calcium phosphate containing phase. The method also includes wherein the functionalized composition further comprises at least one calcium aluminate containing phase that may or may not be functionalized with a linking group, as described herein. The functionalized compositions may be any of the compositions of this invention as described herein.

Another embodiment of this invention provides a method of repairing a void in a bone, vertebrae, or tissue structure in-vitro comprising exposing a void in a patient's bone, vertebrae, or tissue structure by the use of surgery (such surgery techniques and procedures known by those skilled in the art); and placing into the void or encompassing around the void a functionalized composition comprising at least one calcium phosphate containing phase that is functionalized either on the surface of said calcium phosphate containing phase or within a porous scaffold of said calcium phosphate containing phase with a linker group comprising at least one of an organic acid molecule, a phosphonic acid, an amine, N,N-dicyclohexylcarbodiimide, and 3-maleimidopropionic acid N-hydroxysuccinimide ester, and combinations thereof, and one or more of another chemical moiety and/or one or more of a biologically active moiety, wherein the linker group provides for a reactive location for the attachment of either of the another chemical moiety or the biologically active moiety, or both, to the calcium phosphate containing phase, and optionally including wherein at least one of the calcium phosphate containing phases are in a monolithic form, thereby repairing the void of the bone. As will be appreciated by those skilled in the art, other embodiments of this method include employing any of the functionalized compositions as described in this application.

The present invention provides a body or artificial prosthesis for in vitro and in vivo use comprising the functionalized compositions of this invention as described herein. The body or artificial prosthesis of this invention has a porosity suitable for achieving vascularity, and may be in the form of a monolithic structure.

The functionalized body or artificial prosthesis, functionalized compositions, and methods of this invention will be more fully understood from the following descriptions of the invention and the claims appended hereto.

BRIEF DESCRIPTION OF THE DRAWINGS

FIGS. 8-17 Show spectra of various embodiments of the functionalized compositions comprising a calcium aluminate containing phase of the present invention.

FIG. 18 Shows bone implants used to help repair or replace damaged bone.

FIG. 19 Shows a preferable form of the compositions comprising a calcium aluminate containing phase of the present invention and the functionalized "interface" between the "surface" of the compositions and the biologic "tissue".

DETAILED DESCRIPTION OF THE INVENTION

Figure 1A:
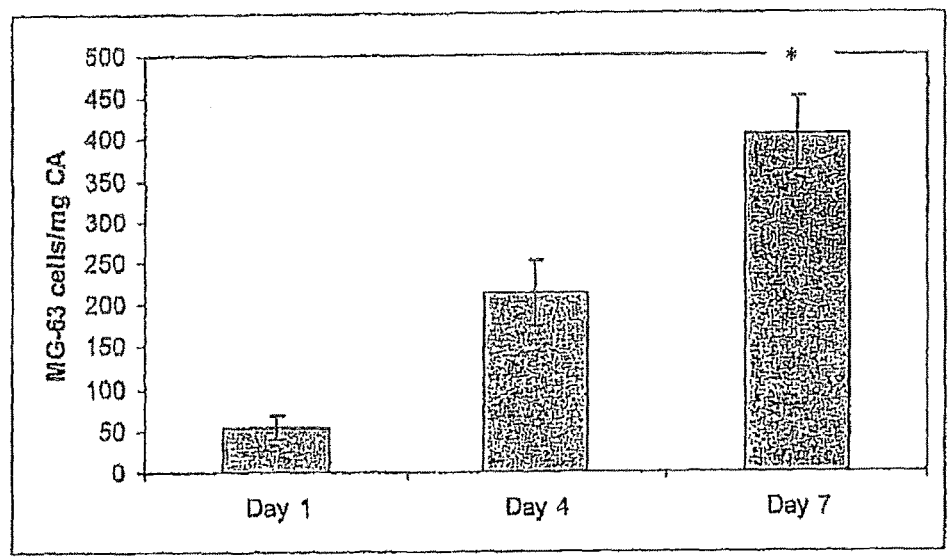
FIG. 1. MG-63 cells attach and proliferate on compositions comprising a calcium aluminate containing phase of the present inventions under static (A) and dynamic (B) culture conditions as assessed by CyQuant assay.

A functionalized composition is provided comprising (1) at least one calcium phosphate containing phase that is functionalized either on the surface of the calcium phosphate containing phase or within a porous scaffold of the calcium phosphate containing phase with a linker group, the linker group comprising at least one of an organic acid molecule, a phosphonic acid, an amine, N,N-dicyclohexylcarbodiimide, and 3-maleimidopropionic acid N-hydroxysuccinimide ester, and combinations thereof, and (2) one or more of another chemical moiety and/or one or more of a biologically active moiety, wherein the linker group provides for a reactive location for the attachment of either of the another chemical moiety or the biologically active moiety, or both, to the calcium phosphate containing phase, and (3) optionally including wherein at least one of the calcium phosphate containing phases is or are in a monolithic form.

As used herein the phrases "at least one" and "one or more" means one or greater than one in number (a plurality), and includes for example but not limited to one, two, three, four, five, and six, and greater in number than six.

As used herein, the terms "monolith", "monolithic form", and "in the form of a monolith" mean an aggregated structure that is bonded together.

As used herein, the phrases "biologically active material" or "biologically active" means a state in which a substance (material or molecule which may or may not be biologically derived) participates in, either positively or negatively, in a natural process. For example, a protein or peptide immobilized on a surface that successfully mediates cell adhesion between cells and the surface is considered "biologically active". Biological activity is determined through the process of a bioassay. Biological activity of materials is well defined and understood by those persons skilled in the art. For example, a biologically active moiety may be defined as those moieties derived from biological sources or small biologically active molecules used as complementary and alternative therapies. Among these biologically active moieties are products derived from botanicals or animals, and include for example but not limited to, fatty acids, amino acids, and proteins, peptides, and antibiotics to name a few. Concerning bone formation, proteins are known osteoinducive factors, and stimulate bone tissue formation and therefore directly bond with bone and thus form a uniquely strong biomaterial-bone interface.

The resulting functionalized compositions of the present invention have the characteristic of a plastic consistency such that the functionalized composition (1) is mechanically pliable by the use of the force of the human hand and (2) adheres to natural bone where it sets (becomes hardened in place) providing mechanical support and bonding of the encompassed bone.

As used herein, the term "plastic" or "plastic consistency" is defined as having the capability of being shaped or formed, such as for example, having the physical properties of a putty like substance which is agglomerated and adheres together but has the characteristics of being pliable and flexible allowing for the substance (for example, the functionalized compositions of the present invention) to be formed into any three dimensional shape or structure or allowing it to encompass or envelope other structures, such as for example but not limited to natural bone, vertebrae, or tissues, by being mechanically "pressed", for example by or under the force of the human hand, or formed around, between, and/or into said structures, preferably when mixed with mixed with a sufficient amount of water (preferably, for example but not limited to, water in the amount from 1 to 50 percent by weight of the functionalized composition).

In another embodiment of the functionalized compositions of the present invention as described herein, the organic acid has a formula of $(CO_2H)_a C_n H_{2n+(-2 \text{ through } +2)} X_d$, wherein X is selected from the group of $CH_3$, $COOH$, $OH$, $NH_2$, and $Br$ and wherein a is a number from about 1 to about 3, wherein n is a number from about 1 to about 1000, and wherein d is a number from about 1 to about 3.

In another embodiment of the present invention, the functionalized composition as described herein, includes wherein the biologically active moiety is at least one selected from the group of a protein, a peptide, and an antibiotic. In a preferred embodiment of this invention, the protein is one or more selected from the group consisting of a collagen, and a transforming growth factor beta superfamily protein. In a preferred embodiment of functionalized compositions of the present invention as described herein, the transforming growth factor beta superfamily protein is one or more of a protein selected from the group consisting of a bone morphogenetic protein and an activin. The bone morphogenetic protein is one selected from the group consisting of a BMP-2, a BMP-2/BMP-7 heterodimer, a BMP-2/BMP-4, a BMP-2a, a BMP-3, a BMP-3b/GDF-10, a BMP-4, a BMP-4/BMP-7 heterodimer, a BMP-5, a BMP-6, a BMP-7, a BMP-8, a BMP-8a, a BMP-9, a BMP-10, a BMP-15/GDF-9B, a BMP-8b, and a decapentaplegic/DPP, and combinations thereof.

In a preferred embodiment of the functionalized compositions of the present invention as described herein, the biologically active moiety is an antibiotic. Preferably, the antibiotic is selected from the group consisting of an ampicillin, a vancomycin, a penicillin, a gentamycin, and an amoxicillin, and combinations thereof.

In another preferred embodiment of the functionalized compositions of the present invention as described herein, the peptide is a RGDC peptide (arginine-glycine-aspartate-cysteine), or is a KRSR peptide (lysine-arginine-serine-arginine), or is a KRSRC peptide (lysine-arginine-serine-arginine-cysteine), or is any cysteine peptide.

The calcium phosphate containing phase of the functionalized compositions of the present invention as described herein includes a calcium phosphate (hereinafter abbreviated as "CaP"). The calcium phosphate may be in any phase, derivative or analog, and may be, for example but not limited, a calcium orthophosphate, a calcium metaphosphate, a calcium pyrophosphate, a hydroxyapatite, and combinations thereof. Most preferably, the calcium orthophosphate is selected from the group consisting of a monocalcium orthophosphate, a dicalcium orthophosphate [$Ca_2(PO_4)_2$], a tricalcium orthophosphate [$Ca_3(PO_4)_2$], and combinations thereof.

In another embodiment of the functionalized compositions of the present invention comprising the calcium phosphate containing phase functionalized with the linker group and including the chemical moiety or biologically active moiety, as described herein, further comprises at least one calcium aluminate phase wherein said calcium aluminate containing phase comprising one or more phases, analogs and derivatives of calcium aluminate that result from the interaction of $C_nA_y$, $C_nA_y$-hydrates, CaO, $Al_2O_3$, $Al_nO_y$-hydrates with or without $P_nO_y^x$ to form CX and/or AX and/or CAX, wherein n is an integer from about 1 to about 12, y is an integer from about 1 to about 24, x is an integer from about 1 to about 12, X is a phosphate moiety, C is CaO, and A is $Al_2O_3$.

In yet another embodiment of this invention, the functionalized compositions further comprise wherein each of the calcium phosphate containing phases is in a monolithic form (in the form of a monolith structure).

In yet another embodiment of the present invention, the functionalized compositions, as described herein, further comprises wherein at least one of the calcium aluminate containing phases is in a monolithic form. In a preferred embodiment, the functionalized compositions include wherein each of the calcium aluminate containing phases is in a monolithic form.

Another embodiment of this invention provides for the functionalized compositions, as described herein, further comprising at least one calcium aluminate containing phase wherein the calcium aluminate containing phase comprising one or more phases, analogs and derivatives of calcium aluminate that result from the interaction of $C_nA_y$, $C_nA_y$-hydrates, CaO, $Al_2O_3$, $Al_nO_y$-hydrates with or without $P_nO_y^x$ to form CX and/or AX and/or CAX, wherein n is an integer from about 1 to about 12, y is an integer from about 1 to about 24, x is an integer from about 1 to about 12, X is a phosphate moiety, C is CaO, and A is $Al_2O_3$, and wherein at least one or more of the calcium aluminate containing phases is or are functionalized either on the surface of said calcium aluminate containing phase or within a porous scaffold of said calcium aluminate containing phase with a linker group comprising at least one of an organic acid molecule, a phosphonic acid, an amine, N,N-dicyclohexyl-carbodiimide, and 3-maleimidopropionic acid N-hydroxy-succinimide ester, and combinations thereof, and one or more of another chemical moiety (other chemical moiety) and/or one or more of a biologically active moiety, wherein the linker group provides for a reactive location for the attachment of either of the another chemical moiety or the biologically active moiety, or both, to the calcium aluminate containing phase.

In a preferred embodiment of the present invention, the functionalized compositions as described herein comprise wherein the calcium phosphate is a dicalcium orthophosphate, the calcium aluminate comprises fifty weight percent of a $CaAl_2O_4$ and fifty weight percent of a $CaAl_4O_7$, and the protein is a bone morphogenetic protein-2, and wherein the bone morphogenetic protein-2 is bound to the dicalcium orthophosphate.

Applicable to all embodiments of the present invention as described herein, the functionalized compositions have a plastic consistency and are pliable with use of mechanical force. The functionalized compositions of the present invention having the pliable physical property will subsequently harden to a monolithic form under ambient (room) temperature conditions within one hour to several hours (for example, a time period from 2 to 4 hours).

Applicable to all embodiments of the present invention as described herein, the functionalized compositions further include wherein either one or more or all of the calcium phosphate containing phases is or are in a monolithic form, and wherein either one or more or all of the calcium aluminate containing phases is or are in a monolithic form. The monolithic form may be in varying sizes or shapes and may be preferably in the size of morsels, as described herein.

In another embodiment of the present invention, the functionalized compositions, as described herein, further comprise a collagen.

In a preferred embodiment of the present invention, the functionalized compositions, as described herein, comprise wherein the calcium phosphate is a dicalcium orthophosphate, the calcium aluminate containing phase comprises fifty weight percent of a $CaAl_2O_4$ and fifty weight percent of a $CaAl_4O_7$, and the antibiotic is a vancomycin, a gentamycin, or an ampicillin, or combinations thereof.

In another preferred embodiment of the present invention, the functionalized compositions, as described herein, comprise wherein the calcium phosphate is a tricalcium phosphate, the calcium aluminate containing phase comprises fifty weight percent of a $CaAl_2O_4$ and fifty weight percent of a $CaAl_4O_7$, and the antibiotic is a vancomycin, a gentamycin, or an ampicillin, or combinations thereof.

In another preferred embodiment of the present invention, the functionalized compositions, as described herein, comprise wherein the calcium phosphate is a tricalcium orthophosphate and the antibiotic is a vancomycin, a gentamycin, or an ampicillin, or combinations thereof.

In another preferred embodiment of the present invention, the functionalized compositions, as described herein, comprise wherein the calcium phosphate is a dicalcium orthophosphate and the protein is a bone morphogenetic protein-2.

In a more preferred embodiment of the present invention, the functionalized compositions, as described herein, comprise wherein the protein is selected from the group consisting of a BMP-2 and a collagen.

In another preferred embodiment of the present invention, the functionalized compositions, as described herein, comprise wherein the functionalized calcium aluminate containing phase has an attached protein, and the functionalized calcium phosphate containing phase has an attached protein, and more preferably wherein the protein is a bone morphogenetic protein, and most preferably wherein the protein is a bone morphogenetic protein-2 (BMP-2). Another embodiment of this invention includes wherein the functionalized compositions, as described herein, further comprise a collagen.

The present invention provides for the functionalized compositions, as described herein, further including a second calcium aluminate containing phase comprising one or more phases, analogs and derivatives of calcium aluminate that result from the interaction of $C_nA_y$, $C_nA_y$-hydrates, CaO, $Al_2O_3$, $Al_nO_y$-hydrates with or without $P_nO_y^x$ to form CX and/or AX and/or CAX, wherein n is an integer from about 1 to about 12, y is an integer from about 1 to about 24, x is an integer from about 1 to about 12, X is a phosphate moiety, C is CaO, and A is $Al_2O_3$, wherein this second calcium aluminate containing is not functionalized (i.e. not modified) with the linker group (as described herein). The addition of this second calcium aluminate (not functionalized) to the functionalized compositions of the present invention increases the rate of set of the functionalized composition resulting in a final functionalized composition having a hard monolithic form or hard monolithic structure forming within the time range of within an hour to two hours depending on the amount of the second calcium aluminate (unmodified form) added to the functionalized composition. In a preferred embodiment, this functionalized composition having this second calcium aluminate (unmodified) addition, further comprises a collagen.

A preferred embodiment of this invention provides a functionalized composition comprising (1) at least one calcium phosphate containing phase that is functionalized either on the surface of the calcium phosphate containing phase or within a porous scaffold of the calcium phosphate containing phase with a linker group comprising at least one of an organic acid molecule, a phosphonic acid, an amine, N,N-dicyclohexylcarbodiimide, and 3-maleimidopropionic acid N-hydroxysuccinimide ester, and combinations thereof, and one or more of another chemical moiety and/or one or more of a biologically active moiety, wherein the linker group provides for a reactive location for the attachment of either of the another chemical moiety or the biologically active moiety, or both, to the calcium phosphate containing phase, and optionally including wherein at least one of the calcium phosphate containing phases is in a monolithic form; (2) a first calcium aluminate containing phase comprising one or more phases, analogs and derivatives of calcium aluminate that result from the interaction of $C_nA_y$, $C_nA_y$-hydrates, CaO, $Al_2O_3$, $Al_nO_y$-hydrates with or without $P_nO_y^x$ to form CX and/or AX and/or CAX, wherein n is an integer from about 1 to about 12, y is an integer from about 1 to about 24, x is an integer from about 1 to about 12, X is a phosphate moiety, C is CaO, and A is $Al_2O_3$, wherein the first calcium aluminate containing phase is functionalized with a linker group comprising at least one of an organic acid molecule, a phosphonic acid, an amine, N,N-dicyclohexylcarbodiimide, and 3-maleimidopropionic acid N-hydroxysuccinimide ester, and combinations thereof, and one or more of another chemical moiety and/or one or more of a biologically active moiety, wherein the linker group provides for a reactive location for the attachment of either of the another chemical moiety or the biologically active moiety, or both, to the first calcium aluminate containing phase; (3) a second calcium aluminate containing phase comprising one or more phases, analogs and derivatives of calcium aluminate that result from the interaction of $C_nA_y$, $C_nA_y$-hydrates, CaO, $Al_2O_3$, $Al_nO_y$-hydrates with or without $P_nO_y^x$ to form CX and/or AX and/or CAX, wherein n is an integer from about 1 to about 12, y is an integer from about 1 to about 24, x is an integer from about 1 to about 12, X is a phosphate moiety, C is CaO, and A is $Al_2O_3$; and (4) a collagen. Preferably, the functionalized composition set forth in this paragraph includes wherein the linker group of the calcium aluminate containing phase is 1,12-dicarboxylic acid, N-hydroxysuccinimide, and N,N-dicyclohexylcarbodiimide, and wherein the biologically active moiety is a vancomycin. More preferably, the functionalized composition set forth in this paragraph includes wherein the linker group of the calcium phosphate containing phase is 1,12-dodecanedicarboxylic acid, the biologically active moiety is a biomorphogenetic protein-2, and wherein the calcium phosphate containing phase is in a monolithic form of dicalcium orthophosphate and hydroxyapatite. Most preferably, the functionalized composition set forth in this paragraph includes wherein the second calcium aluminate containing phase is either (i) fifty weight percent of a $CaAl_2O_4$ and fifty weight percent of a $CaAl_4O_7$, or (ii) ninety nine weight percent of a blend of equal parts by weight of a $CaAl_2O_4$ and a $CaAl_4O_7$ and one weight percent of a $C_{12}A_7$.

Another embodiment of the present invention provides a functionalized composition comprising (1) a first calcium aluminate containing phase that is at least one calcium aluminate phase comprising one or more phases, analogs and derivatives of calcium aluminate that result from the interaction of $C_nA_y$, $C_nA_y$-hydrates, CaO, $Al_2O_3$, $Al_nO_y$-hydrates with or without $P_nO_y^x$ to form CX and/or AX and/or CAX, wherein n is an integer from about 1 to about 12, y is an integer from about 1 to about 24, x is an integer from about 1 to about 12, X is a phosphate moiety, C is CaO, and A is $Al_2O_3$; (2) a second calcium aluminate containing phase that is at least one calcium aluminate phase comprising one or more phases, analogs and derivatives of calcium aluminate that result from the interaction of $C_nA_y$, $C_nA_y$-hydrates, CaO, $Al_2O_3$, $Al_nO_y$-hydrates with or without $P_nO_y^x$ to form CX and/or AX and/or CAX, wherein n is an integer from about 1 to about 12, y is an integer from about 1 to about 24, x is an integer from about 1 to about 12, X is a phosphate moiety, C is CaO, and A is $Al_2O_3$, wherein the second calcium aluminate phase is functionalized either on the surface of said calcium aluminate containing phase or within a porous scaffold of said calcium aluminate containing phase with a linker group comprising at least one of an organic acid molecule, a phosphonic acid, an amine, N,N-dicyclohexylcarbodiimide, and 3-maleimidopropionic acid N-hydroxysuccinimide ester, and combinations thereof, and one or more of another chemical moiety and/or one or more of a biologically active moiety, wherein the linker group provides for a reactive location for the attachment of the another chemically active moiety and/or the biologically active moiety, or both, to the calcium phosphate containing phase, and optionally including wherein either the first calcium aluminate containing phase, the second calcium aluminate containing phase, or both of the first and the second calcium aluminate containing phases is or are in a monolithic form. In another embodiment of the present invention as set forth in this paragraph, the functionalized composition further comprises at least one calcium phosphate containing phase. In a preferred embodiment of the invention as set forth in this paragraph, the functionalized composition further comprises at least one calcium phosphate containing phase that is functionalized either on the surface of the calcium phosphate containing phase or within a porous scaffold of the calcium phosphate containing phase with a linker group comprising at least one of an organic acid molecule, a phosphonic acid, an amine, N,N-dicyclohexylcarbodiimide, and 3-maleimidopropionic acid N-hydroxysuccinimide ester, and combinations thereof, and one or more of another chemical moiety and/or of one or more of a biologically active moiety, wherein the linker group provides for a reactive location for the attachment of the another chemically active moiety and/or the biologically active moiety, or both, to the calcium phosphate containing phase, and optionally including wherein at least one of the calcium phosphate containing phases is in a monolithic form. In a more preferred embodiment of the invention as set forth in this paragraph, the functionalized composition includes wherein the first calcium aluminate containing phase is fifty weight percent of a $CaAl_2O_4$ and fifty weight percent of a $CaAl_4O_7$ and wherein the second calcium aluminate containing phase is fifty weight percent of a $CaAl_2O_4$ and fifty weight percent of a $CaAl_4O_7$. Preferably, the functionalized composition includes equal parts by weight of the first calcium aluminate containing phase and of the second calcium aluminate containing phase.

Another embodiment of this invention provides a method of making an artificial prosthesis comprising mapping a patient's identified bone, vertebrae, or tissue structure; creating a three dimensional pattern of the identified bone, vertebrae, or tissue structure from the mapped bone, vertebrae or tissue structure; and either (1) creating a mold or negative of the identified bone, vertebrae, or tissue structure from said pattern; and casting a functionalized composition into said mold thereby forming the artificial prosthesis, or (2) forming a three dimensional structure by hand of the identified bone, vertebrae, or tissue structure from said pattern employing a functionalized composition thereby forming the artificial prosthesis, wherein the functionalized composition comprises a calcium phosphate containing phase (as described herein) that is functionalized with a linker group comprising at least one of an organic acid molecule, a phosphonic acid, an amine, and N,N-dicyclohexylcarbodiimide, and at least one or more of another chemical moiety (molecule or compound) or at least one or more of a biologically active moiety, wherein the linker group provides for a reactive location for the attachment of the another chemical moiety, or the biologically active moiety, or both, to the calcium phosphate containing phase. In a preferred embodiment, the method as described herein includes wherein an antibiotic, protein, or peptide, or combinations thereof, is/are the moiety(ies) attached to the calcium phosphate containing phase. The method also includes wherein the functionalized composition further comprises at least one calcium aluminate containing phase that may or may not be functionalized with a linking group, as described herein. The functionalized compositions may be any of the compositions of this invention as described herein.

Another embodiment of this invention provides a method of repairing a void in a bone, vertebrae, or tissue structure in-vitro comprising exposing a void in a patient's bone, vertebrae, or tissue structure by the use of surgery (such surgery techniques and procedures known by those skilled in the art); and placing into the void or encompassing around the void a functionalized composition comprising at least one calcium phosphate containing phase that is functionalized either on the surface of said calcium phosphate containing phase or within a porous scaffold of said calcium phosphate containing phase with a linker group comprising at least one of an organic acid molecule, a phosphonic acid, an amine, N,N-dicyclohexylcarbodiimide, and 3-maleimidopropionic acid N-hydroxysuccinimide ester, and combinations thereof, and one or more of another chemical moiety and/or one or more of a biologically active moiety, wherein the linker group provides for a reactive location for the attachment of either of the another chemical moiety or the biologically active moiety, or both, to the calcium phosphate containing phase, and optionally including wherein at least one of the calcium phosphate containing phases are in a monolithic form, thereby repairing the void of the bone. As will be appreciated by those skilled in the art, other embodiments of this method include employing any of the functionalized compositions as described in this application.

Calcium aluminate and its representative phases, analogs, and derivatives (including such as for example the introduction of phosphate containing phases resulting from the interaction of $C_nA_y$, $C_n A_y$-Hydrates, CaO, $Al_nO_y$, and $Al_nO_y$-hydrates with $P_nO_y^x$— referred herein as "CAX") are better alternatives as an artificial material, wherein preferably, n is an integer from about 1 to 12 and y is an integer from about 1 to 24, and x is an integer from about 1 to 12. There are several reasons for this including the fact that $C_nA_y$ contains hydratable compounds that introduce needed strength into the matrix via a dissolution/precipitation reaction. Porosity is easily introduced into the structure via the aggregate itself and/or through the use of a foaming agent. The resulting matrix can be cast to a specific shape with ease using casting technology known by those persons skilled in the art, such as including, slip casting, slurry casting or vibration casting into molds to generate a desired shape. The resulting calcium aluminate containing composition is chemically compatible with bone and other biological processes. The resulting shape having the calcium aluminate containing composition can be high fired to make it unreactive with its environment, if desired, or, it can be partially fired to leave it somewhat active, or it may be unfired. Preferably, the calcium aluminate containing phases of the present functionalized compositions are unfired. Furthermore, a hollow cavity within the structure can be created to better allow vascularity to occur and to allow marrow to exist if indeed the body will begin to produce it with the presence of vascularity. Both conditions of vascularity and marrow growth will foster the progress of each process.

The present invention provides an artificial prosthesis having the $C_nA_y$ material as a structure to support tissue growth. It can be pre-engineered to match the desired finished structure and in addition, in the form of hydrates, these materials will slowly be metabolized by the body. Because of the nature of the compounds, they can easily be derivatized and functionalized for use with biological processes, such as for example, but not limited to, accommodating protein building blocks, and binding sites.

The present invention provides artificial prosthesis structures and a method for the manufacture of an artificial prosthesis. The method includes mapping the structure of interest by digitizing data from MRI scans (if soft tissue), X-ray data (if bone structure) or a combination of both, digitizing the data to create a three dimensional pattern or blank of the structure as known by those skilled in the art, utilizing the blank or pattern to create a mold or negative of the structure of interest, casting within the mold the compositions of the present invention comprising the $C_nA_y$, CAX, and/or derivatives, and/or analogs of $C_nA_y$ or CAX, of this invention, and optionally adding biologically active materials to produce an artificial prosthesis. Optionally, the resulting artificial prosthesis is then further processed, if desired. This may involve a firing process to fix certain desired mineralogical phases and/or chemically activated by an immersion process known by those persons skilled in the art.

The present invention provides a functionalized body for in vitro and in vivo use comprising then functionalized compositions comprising at least one calcium phosphate containing phase and optionally at least one calcium aluminate containing phase, all as described herein. In preferred embodiments of this invention the calcium aluminate containing phase further comprises one of a foaming agent, a fiber, an accelerator, a retarder, a surfactant, and a reactive alumina, and combinations thereof.

In another embodiment of this invention the functionalized body as described herein includes wherein the calcium aluminate containing phase comprises one or more phases, analogs and derivatives of calcium aluminate.

In a preferred embodiment of this invention, the functionalized body as described herein includes wherein the calcium aluminate containing phase results from the interaction of $C_nA_y$, $C_nA_y$-hydrates, CaO, $Al_nO_y$-hydrates with $P_nO_y^x$ to form CAX, wherein n is an integer from about 1 to about 12, y is an integer from about 1 to about 24, and x is an integer from about 1 to about 12.

In another embodiment of this invention, a composition is provided that comprises a calcium aluminate containing phase and optionally at least one or more of a retarder, and a surfactant, wherein the calcium aluminate containing phase results from the interaction of $C_nA_y$, $C_nA_y$-hydrates, CaO, $Al_nO_y$-hydrates with $P_nO_y^x$ to form CAX, wherein n is an integer from about 1 to about 12, y is an integer from about 1 to about 24, and x is an integer from about 1 to about 12. The composition optionally further comprises at least one of a fiber, water, an accelerator, and a reactive alumina, and combinations thereof.

In yet another embodiment of this invention, a method is provided for using a composition for producing artificial structures for use in-vitro or in-vivo by a patient comprising employing the functionalized compositions of the present invention. The present composition may also be used as an in-situ patch for repairing a bone void of the patient that may occur, for example but not limited to, as a result of trauma and injury to the bone.

The present invention includes the calcium phosphate and the optional calcium aluminate biomaterials as described herein that have been modified by, such as for example, an organic acid to enable the attachment of other moieties thereto such as for example antibiotics, peptides or proteins. More specifically, the resulting body or artificial prosthesis comprises the functionalized compositions of the present invention having the modified calcium phosphate containing phase and optionally the modified calcium aluminate containing phase and human adult mesenchymal stem cells (hAMSC) and/or osteo-blast like MG-63 cells that are attached to the body or artificial prosthesis that has been modified by the organic acid.

Figure 20:
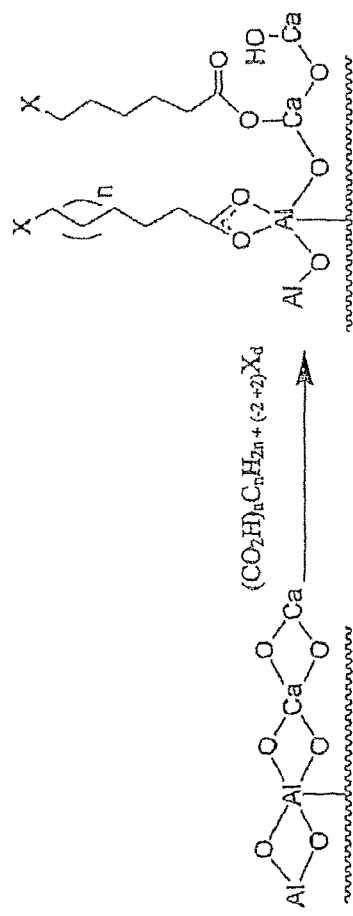
FIG. 20 shows that by varying the functionality of the head and tail groups of acids used as linkers that the calcium aluminate containing compositions may be modified in many ways to provide reactive locations for attachment of other chemical moieties and/or biologic moieties.
Figure 21:
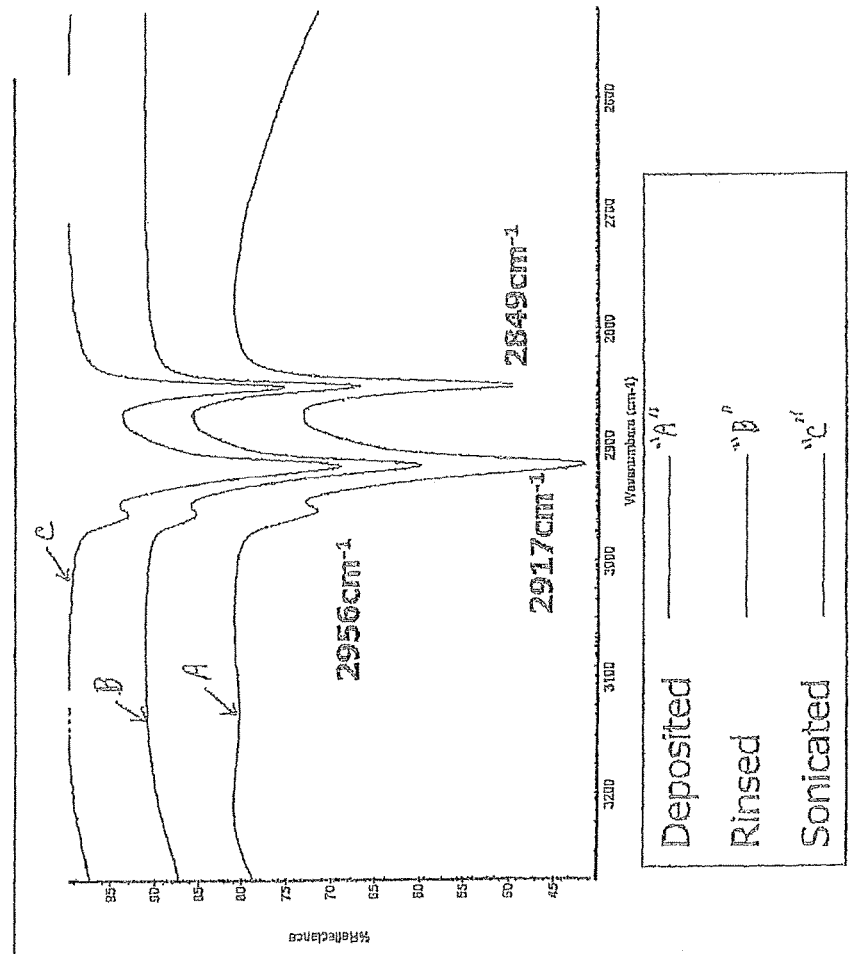
FIG. 21 shows phosphonic acid as the linker to functionalize the calcium aluminate containing phase of the compositions of this invention.
Figure 22:
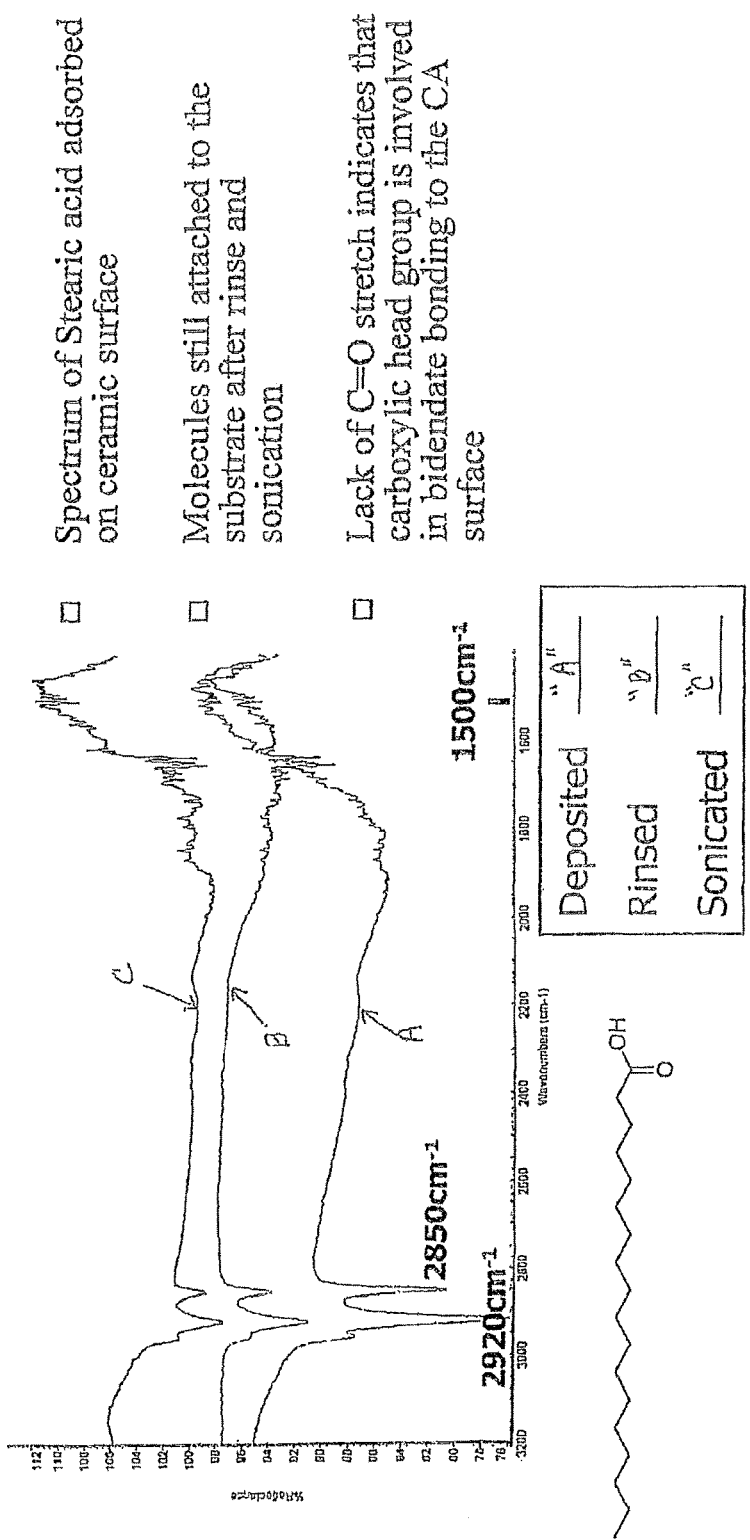
FIG. 22 shows an example of carboxylic acid binding onto the surface of a calcium aluminate containing composition of this invention. The spectra shown is that of stearic acid absorbed on the surface of a calcium aluminate containing composition.
Figure 23:
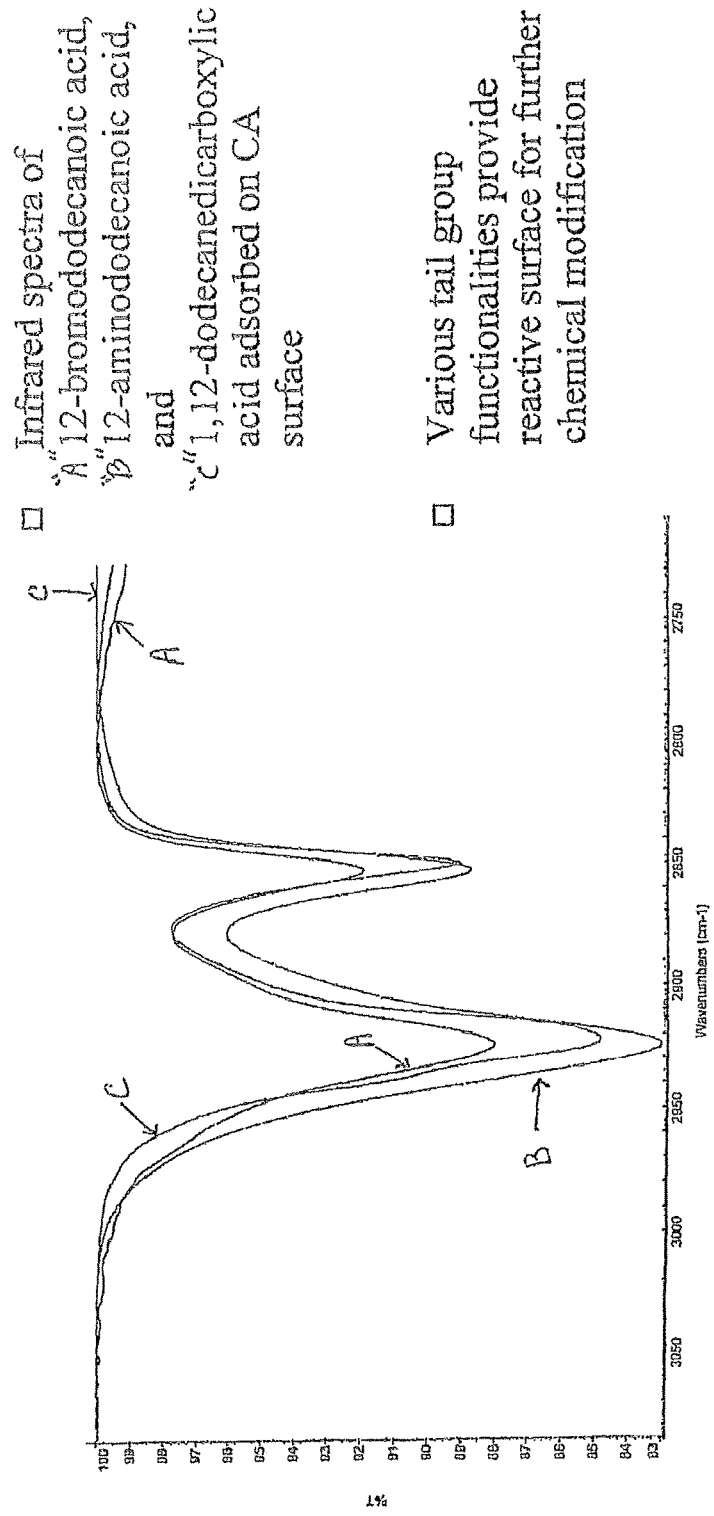
FIG. 23 shows the functionalization of a calcium aluminate containing composition of this invention with organic acid tail group variations.

The modification of the body or artificial prosthesis or the functionalized compositions of the present invention that have been modified by organic acids enhances the ability of the body, the prosthesis, or the compositions to act as a bone stabilizer. Organic acids were used as the modifiers (linkers) and were found to bind irreversibly to the body, prosthesis, and compositions set forth herein. The organic acid modifiers (linkers) employed in the functionalization of the body, prosthesis, and compositions of this invention are molecules comprising a head group with a pKa less than about 15, such as for example but not limited to phosphonic acid, carboxylic acid, and amines, followed by an alkyl chain, and a variable tail group. The functionality of the tail group may be varied so that the organic acid modifier may act as a linker between the body, prosthesis, or compositions of the present invention, and other organic or biologic molecules of choice. The organic acid modifier is bound to the body, prosthesis, or compositions of the present invention and can not be removed by chemical or mechanical agitation. The attachment is preferably done post-production of the body but may be done prior to the production of the formed body. With regard to the composition(s) comprising the calcium phosphate and optionally the calcium aluminate containing phase(s) of this invention, the attachment of the linking group may be performed prior to or post formation of the three dimensional shape. FIG. 20 shows the reaction between the compositions comprising a calcium aluminate containing phase, the organic acid linking group (which may preferably have the formula shown in FIG. 20 or more preferably the formula $(CO_2H)_aC_nH_{2n+(-2\ through\ +2)}X_d$, wherein X is selected from the group of $CH_3$, COOH, OH, $NH_2$, and Br and wherein a is a number from about 1 to about 3, wherein n is a number from about 1 to about 1000, and wherein d is a number from about 1 to about 3, and wherein X is the variable tail group, and the resulting attachment of the organic linker to the compositions of this invention. It will be appreciated that multiple functionalities may be deposited in solution with a ratio, for example but not limited to, preferably 50:50, —COOH:Br tails. The organic functionalization of the compositions comprising a calcium phosphate and optionally a calcium aluminate containing phase adds chemical variabilility to the modified compositions by presenting chemically reactive groups at the interface of the pores and surface with the environment in which the modified composition is located.

The tail groups "X" as described herein may be used for several purposes. For example, the variation of the tail group may be used to control and tailor the body's interfacial properties such as for example but not limited to hydrophobicity. The tail group may also be reacted further with other organic molecules to tether small molecules or macromolecules to the body or compositions of the present invention in order to control the body's or composition's properties and function. Further, the tether may serve a delivery function by allowing for the deposition of desired organics to a specific location, especially in biologic applications. These molecules may include for example, but are not limited to, polymers, peptide sequences, proteins, antibiotics, and blood thinning pharmaceuticals.

The modified body and compositions of the present invention may be used as bone stabilization materials. The organic molecule functionalization of the body and compositions as described herein brings added value due to the flexibility of the method which allows for the attachment of many different types of molecules that may be useful in a biological setting.

The modified body and modified calcium phosphate and modified calcium aluminate compositions of the present invention may be hydratable or nonhydratable, and may be useful as a bone void filler, a bone graft extender, a three dimensional resorbable tissue scaffold, and as an implant such as for example a long bone replacement and/or repair. The modified body and modified calcium phosphate and modified calcium aluminate containing compositions of the present invention have biocompatibility as demonstrated by human adult mesenchymal stem cells, embryonic chick chorioallantoic membrane assay, and rat calvarial defect animal testing. The ease of casting and the strength and porosity of the body of the present invention are advantages over current bone graft technologies and will be useful in combat support and military medical centers. It will be appreciated that the functionalized compositions of the present invention may be manufactured having different synthetic conditions with varying porosities, hydratability and surface roughness, for example.

The functionalized compositions of the present invention with controlled porosity and high strength show potential as bone replacement materials. Our results indicate that the functionalized compositions of the present invention are biocompatible with human MG-63 osteoblast-like cells and human adult mesenchymal stem cells in both dynamic and static in vitro culture conditions.

Figure 26:
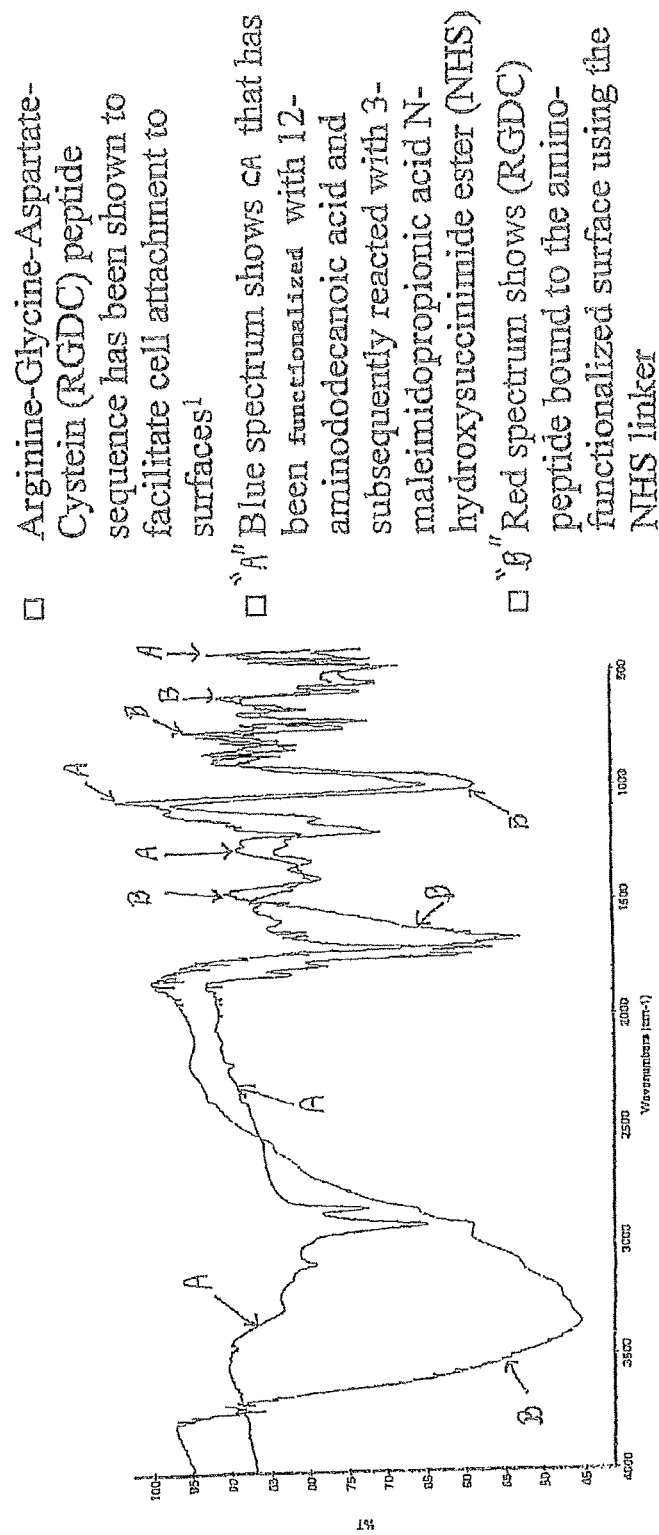
FIG. 26 shows RGDC peptide coupling to an amino-functionalized calcium aluminate containing composition of this invention.
Figure 27:
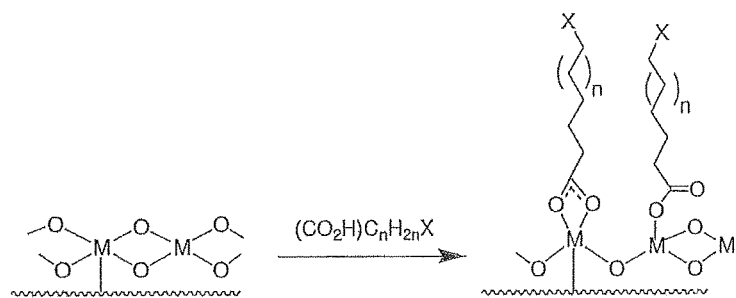
FIG. 27 shows a reaction scheme of an embodiment of the modification of the calcium aluminate material of this invention.

FIGS. 20-26 show examples of molecules that may be attached to the body or the calcium aluminate containing compositions or calcium aluminate materials of the present invention. As used herein, these molecules are referred to as a linker(s), a linker group, a linking group, a modifier, or as a coupling agent, and are at least one of an organic acid, a phosphonic acid, an amine, and/or a N,N-dicyclohexylcarbodiimide. For example, but not limited to, the following molecules are a linker, a linking group, or a coupling agent that may be attached to the body or the calcium aluminate containing compositions of this invention: Octadecylphosphonic acid, Octadecylcarboxylic acid, Octadecylamine, 12-romododecanoic acid, 1,12-dodecanodicarboxylic acid, 16-hydroxyhexadecanoic acid, and 12-aminododecanoic acid. The reaction scheme set forth in FIG. 27 shows one embodiment of the modication of the calcium aluminate material of the present invention.

Figure 28:
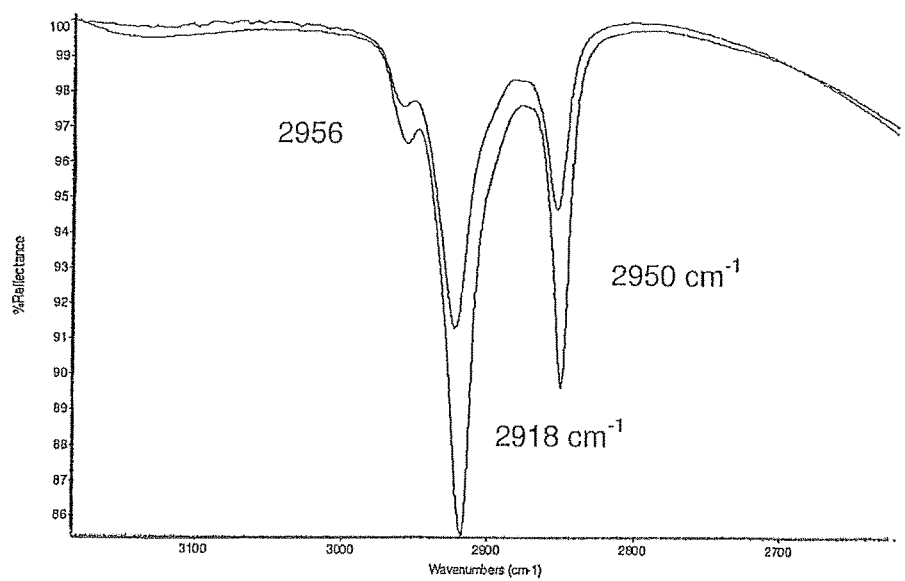
FIG. 28 shows an infrared spectra of the C—H region of a calcium aluminate material of the present invention functionalized with octadecylcarboxylic acid.

FIG. 28 shows the infrared spectra of the C—H region of a calcium aluminate material of the present invention functionalized with octadecylcarboxylic acid. More specifically, FIG. 28 shows the infrared spectra of the C—H region for a calcium aluminate material of the present invention modified with octadecylcarboxylic acid attached to it through the carboxylic acid head group. The peaks set forth in the graph of FIG. 28 are due to C—H stretching of the $CH_2$ groups in the alkyl chain and the $CH_3$ terminus (2956 $cm^{-1}$). In FIG. 28, the blue spectra, labeled "A", is before rinsing and the red spectra, labeled "B", is after rinsing.

Examples of organic molecules that may be tethered to the surface of the calcium aluminate materials of the present invention include 3-maleimidopropionic acid N-hydroxysuccinimide ester, Dicyclohexylcarbodiimide, Arginine-Glycine-Aspartic Acid-Cysteine attached via 3 maleimido - - - to 12-aminododecanoic acid (see figure immediately below), and Ampicillin via dicyclohexylcarbodiimide coupling on 1,12 dodecanedicarboxylic acid.

Figure 29:
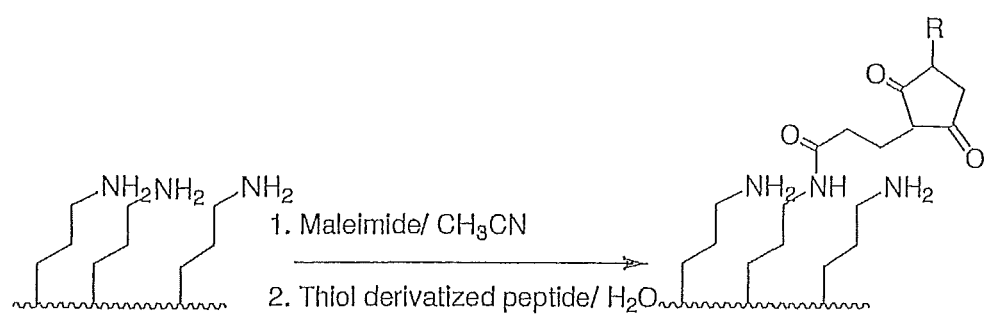
FIG. 29 shows a reaction scheme of maleimide coupling of cysteine derivatized peptides to the surface of calcium aluminate material of the present invention.

FIG. 29 reaction scheme shows maleimide coupling of cysteine derivatized peptides to the surface of calcium aluminate material of the present invention.

All molecules were initially adhered to the surface of the calcium aluminate materials of the present invention using a 1 hr dip in a 1 mM-10 mM solution of organic and THF (tetrahydrofuran), followed by 30 minutes to about 1 hour in a 120 degrees C. (Centigrade) oven. Rinsing consists of rinsing the solvents in THF and then sonicating them for 30 minutes in THF.

The maleimide coupling procedure is set forth in the reaction set forth immediately above and is followed by evacuation of solvent at 0.1 Torr. This coupling procedure, for example, may be employed for thiol or cysteine derivatized molecules such as peptides and proteins.

The DCC coupling procedure, known by those skilled in the art, may also be employed to link carboxylic acid terminated molecules to molecules with a reactive —OH group.

The present invention employs coupling procedures to attach molecules to the body or compositions comprising a calcium aluminate containing phase of this invention via a OH, NH2, COOH, or Br reactive tail group. It will be appreciated by those persons skilled in the art that this procedure allows access to SN2 chemistry, amide coupling, and Michael additions (via maleimide), for example.

Those persons skilled in the art will appreciate that the persistence of the $CH_2$ groups in the IR spectra confirms that the alkyl chain is still present on the surface of the modified calcium aluminate materials of the present invention after chemical and mechanical agitation.

We have tested MG-63 (osteoblast-like cells) and human adult mesenchymal stem cells without inducing them into osteoblasts and inducing them into osteoblasts through serum additives. It will be appreciated that the modified porous body and the modified calcium aluminate materials of the present invention improve their effectiveness as biomaterials. The adhesion and bonding of various molecules, for example, but not limited to, long chain alkanes, with different head and tail functional groups to the surface of ceramics were tested and the results set forth herein and in the attached figures (see especially FIGS. 19-26). The surfaces of the modified calcium aluminate materials of this invention were analyzed with diffuse reflectance infrared fourier transform spectroscopy (DRIFT). Additionally, the surface of the modified calcium aluminate material of this invention has been functionalized with antibiotic molecules.

Attachment, proliferation, and viability of MG-63 cells and hAMSC were assessed using the CyQuant assay, scanning electron microscopy, and fluorescent viability stains. The viability of cells when attached to the body of the present invention is above 90%, and cells proliferate when attached to the calcium aluminate surface.

Over the course of 14 days in an osteogenic supplement, differentiation is visible as indicated by increased alkaline phosphatase activity, a marker for osteoblast differentiation. In vivo chick chorioallantoic membrane (CAM) assays also indicate the biocompatibility of calcium aluminate. This suggests that the functionalized compositions, functionalized prosthesis, and/or the functionalized bodies of the present invention may be implanted into rat calvarial defects. Based on the in vitro and preliminary in vivo studies, calcium aluminate-based materials of the present invention are an effective material for bone regenerative medicine. Calcium aluminates of the present invention are biocompatible and can be used in bone tissue engineering, when seeded with human adult mesenchymal stem cells differentiated into osteoblasts. This study focuses on the use of the calcium aluminate materials of the present invention as a bone substitute, however, as a scaffolding material, the calcium aluminate materials of the present invention may be used to support a variety of other cell types including such as for example but not limited to nerve and organ tissues.

The functionalized compositions of the present invention may be employed as a bone replacement material. The calcium aluminate materials of the present invention having controlled porosity, and high strength, and their ease of forming complex three-dimensional shapes, overcome many of the difficulties associated with the background technology. Functionalized compositions of the present invention in the form of morsels were chosen as the material for use as a bone void filler, as set forth in the examples.

We have developed a novel method to produce the functionalized compositions of the present invention that is inexpensive, relatively easy, and economical. In our preparation of the calcium phosphates and calcium aluminates of the present invention, we are able to control phase composition, micro-porosity, surface texture and dissolution rate. Through our novel approach we are synthesizing compositions comprising a calcium phosphate phase and a calcium aluminate containing phases with defined and controlled macro-porosity and volume stability.

The cellular assessment of calcium aluminate materials for bone tissue engineering is set forth herein. We have studied the biocompatibility of calcium aluminates through the attachment and proliferation of MG-63 cells and human adult mesenchymal stem cells on the calcium aluminate materials of the present invention. MG-63 cells are an osteo-blast like cell line. Bone marrow-derived human adult mesenchymal stem cells (hAMSC) are a population of multi-potent cells with the ability to differentiate into osteogenic cells. Given that hAMSC can be directed into the osteogenic lineage in vitro in the presence of a dexamethasone-containing osteogenic supplement, we have also evaluated osteoblastic differentiation of hAMSC on the calcium aluminate material of the present invention.

In a more preferred embodiment of this invention, the functionalized compositions as described herein is functionalized with an organic acid and subsequently reacted with 3-maleimidopropionic acid N-hydroxysuccinimide ester (NHS) for binding one or more peptides to an amino-functionalized calcium aluminate containing phase.

The functionalized body may be an artificial prosthesis wherein the artificial prosthesis is selected from the group consisting of an artificial bone, artificial joint, in-vitro support structure, an in-vivo support structure, and a scaffolding matrix for support of cell, tissue, organ, and nerve growth.

In a more preferred embodiment of this invention, the functionalized composition as described herein includes wherein an antibiotic is the moiety attached to the calcium aluminate containing phase. The antibiotic may be any antibiotic, such as for example but not limited to ampicillin or vancomycin. The present modified compositions comprising a calcium aluminate containing phase provides for the localized delivery of antibiotic to a specific area of a patient's body. This is beneficial since amount and concentration of the localized delivered antibiotic may be increased in a manner not possible with employing the traditional systemic delivery routes of antibiotic administration such as oral medications, and intravenous and intramuscular therapies. It is well known by those skilled in the art that systemic delivery of antibiotics shall attack bacteria throughout the body including for example the bacteria flora needed for maintaining a healthy gastrointestinal tract. The modified compositions of the present invention provide for the effective delivery of antibiotics to a specific localized area of a patient's body in high concentration without adversely effecting the beneficial bacteria located in other parts of the patient's body. As used herein the term "patient" refers to all members of the animal kingdom including for example but not limited to human beings.

In yet another embodiment of this invention, the functionalized compositions as described herein comprise at least one of a retarder, water, an accelerator, a surfactant, a foaming agent, a fiber, and a reactive alumina, and combinations thereof.

In a more preferred embodiment of this invention, the functionalized composition as described herein further comprises a calcium aluminate containing phase that is functionalized with an organic acid and subsequently reacted with 3-maleimidopropionic acid N-hydroxysuccinimide ester (NHS) for binding one or more peptides to an amino-functionalized calcium aluminate containing phase.

The following examples demonstrate the instant invention in greater detail. These examples are not intended to limit the scope of the invention in any way.

Example 1

|  | Wt. % |
| --- | --- |
| Calcium Aluminate (various phases) | 99 |
| Citric Acid Monohydrate | 0.2 |
| Castament FS20 | 0.55 |
| Herculon 153 fibers | 0.25 |
| Water (for casting as a 'plus' addition) | 22.0 |

In this example an inert mold of the object would be created from the three dimensional data. Common mold materials are aluminum, steel, PVC or polyurethane. Water would be added to the above mix to give it a vibration cast consistency. This mix would then be vibrated into the mold. In other examples the water addition, additives and consistency of the material could be adjusted to allow for slip casting or gel casting. The water demand of the mixture is controlled by the particle size distribution of the mix and also the surfactant (in Example 1, Castament FS20). Examples of other surfactants are, but not limited to, sodium tripolyphosphate (STP or STPP), Darvan #7, and Melflux. As will be understood by those persons skilled in the art, the choice of surfactant shall affect the water demand and associated additive concentrations such that they will need to be adjusted, accordingly. In examples 1-4, water added was kept constant in order to compare other resulting properties. A typical water range can be from about 5%-75%.

The material would be allowed to 'set' (precipitation of the calcium aluminate-hydrate phases). The speed of this reaction is slowed by the addition of citric acid monohydrate. Other materials that can control the reaction or 'set' time are, for example but not limited to, boric acid and anhydrous citric acid (as retarders) and lithium carbonate, sodium silicate or sodium aluminate (as accelerators).

The 'set' results in a shape exhibiting strong mechanical properties in a mechanism very similar to that of concrete. The mold would then be stripped and the shape and dried in an oven at approximately 110 degrees Celsius (C). In this form the shape would be composed of various calcium aluminate phases and calcium aluminate hydrate phases, alumina gel, alumina (present in the calcium aluminate starting material), Herculon 153 fibers (given as an example but substitution of biocompatible fiber can be accomplished). Typically this shape would now be fired at about 1000° C. During the firing process the calcium aluminate-hydrates and alumina gel will be converted to the unhydrated phases (primarily CA and $CA_2$) and the alumina gel will convert to the oxide. This process will also introduce porosity in place of the chemically combined water and the organic fiber. The organic fiber is introduced to allow for interconnected porosity after burn-out. The diameter of the resulting channels is determined by controlling the diameter of the starting fiber. The presence of the fiber also gives water a pathway of escape from the shape, although this is not critical in small shapes. The resulting shape is suitable as scaffoldings or as an artificial bone structure capable of supporting stem cells that will differentiate into osteoblasts (in the case of bone). In addition, this structure can now be chemically altered to accommodate binding of proteins or other bioactive factors, promoting bone growth, for example. Once introduced in vivo, the matrix will again begin to hydrate which will allow bio-decomposition to occur while natural bone is being formed. If during the firing process, the shape is exposed to temperatures from 1400 degrees C. (Centigrade) to about 1650 degrees C., and preferably near 1550 degrees C., $CA_6$ will be formed and re-hydration will not occur. In some cases this may be desirable, for example hip replacement, where a well defined geometric structure needs to be maintained.

Further, in another embodiment of this invention, the calcium aluminate phases of the composition of this invention have the characteristic of a plastic consistency such that the calcium aluminate containing phases are mechanically pliable by the use of the human hand and may be formed in any desired shape without the use of a mold. The calcium aluminate containing phases adhere to natural bone where it sets (becomes hardened in place) providing mechanical support and bonding of the encompassed bone.

A variety of other compositional examples are given here with a short explanation of possible benefits.

Example 2

|  | Wt. % |
|---|---|
| Calcium Aluminate (various phases) | 84 |
| Citric acid monohydrate | 0.2 |
| Reactive aluminas | 15 |
| STPP | 0.55 |
| Herculon 153 fibers | 0.25 |
| Water (for casting as a 'plus' addition) | 22.0 |

In this example reactive aluminas such as ALMATIS' A-2, A-3000 and A-1000 are added to give improved casting character and a denser, less porous final matrix. Herculon 153 fibers are fibrous materials commercially available from Hercules, Incorporated, Wilmington, Del. Darvan #7 is a sodium polymethacrylate composition used as a surfactant and is commercially available from R. T. Vanderbilt Company, Inc., Norwalk, Conn.

Example 3

|  | Wt. % |
|---|---|
| Calcium Aluminate (various phases) | 98.5 |
| Foaming agent | 1.0 |
| Darvan #7 | 0.5 |
| Water (for casting as a 'plus' addition) | 22.0 |

In this example a foaming agent such as CF-500 or CF-700 from Unifoam, is used to introduce a high degree of porosity to the finished material. The diameter of the porosity can be controlled by the choice of foaming agent (e.g. CF-700 gives a larger bubble) and the volume of porosity is controlled by the amount of foaming agent added.

Example 4

|  | Wt. % |
|---|---|
| Calcium Aluminate (various phases) | 90.5 |
| Foaming agent | 1.0 |
| Calcium orthophosphate | 8.0 |
| Melflux | 0.5 |
| Water (for casting as a 'plus' addition) | 22.0 |

In this example a phosphate source is added to give raw material for osteoblast precipitation of natural bone. Melflux is a polymeric surfactant commercially available from Degussa Construction Polymers, Kennesaw, Ga.

As can be seen in these examples there are a variety of strategies one can take in determining an appropriate starting matrix. The examples set forth herein are given to demonstrate this breadth, however, they are not intended to limit the scope of the present invention as described herein. These examples set forth herein are for the purposes of illustration and it will be evident to those persons skilled in the art that numerous variations and details of the instant invention may be made without departing from the instant invention as set forth herein.

Detailed Compositional Strategy, Example 5

Example 5 will be used to demonstrate a detailed compositional matrix and the resulting physical properties of the resulting solid body.

Calcium Aluminate Clinker of the following chemistry (reported on an oxide basis) was obtained for the study. The material was screened, sized and chemistry was determined on each fraction (see table I below)

|  | Fraction | | | |
|---|---|---|---|---|
|  | +10 m | 10/28 m | 28/65 m | −65 m |
| Oxide | (concentration in Wt %) | | | |
| $SiO_2$ | 0.44 | 0.29 | 0.22 | 0.25 |
| $Al_2O_3$ | 71.59 | 71.21 | 70.35 | 71.19 |
| $Fe_2O_3$ | 0.07 | 0.01 | <0.01 | 0.01 |
| CaO | 27.38 | 28.08 | 29.02 | 27.95 |
| MgO | 0.27 | 0.22 | 0.21 | 0.31 |
| $Na_2O$ | 0.23 | 0.17 | 0.18 | 0.26 |
| $K_2O$ | 0.01 | 0.01 | 0.01 | 0.02 |
| $P_2O_5$ | 0.01 | 0.01 | 0.01 | 0.01 |

Mineralogical Examination of these fractions showed the following:

| Compound | +10 m | 10/28 m | 28/65 m | −65 |
|---|---|---|---|---|
| | | Present | | |
| CaAl2O4 (CA) | M | M | M | M |
| CaAl4O7 (CA2) | M | M | M | M |
| Ca12Al14O33 (C12A7) | m | m | t | nd |
| Ca3Al2O6 (C3A) | nd | nd | nd | nd |
| Ca5Al6O14 (C5A3) | nd | nd | nd | nd |
| Ca2Al12O5 (C2A) | nd | nd | nd | nd |
| CaAl12O19 (CA6) | nd | nd | nd | nd |
| Ca3Al10O18 (C3A5) | nd | nd | nd | nd |
| CaO (C) | t | t | t | t |
| Al2O3 (A) | t | t | t | t |

M = Major (greater than or equal to 50%),
m = minor (greater than zero but less than 50%),
t = trace,
nd = not detected.

This chemistry and mineralogy is typical for a 70% alumina containing calcium aluminate cement. calcium aluminate cements containing greater than 70% alumina can be used. Calcium aluminate cement containing less than 70% alumina can also be used; however, most commercially available products have impurities, which increase in concentration as the alumina content decreases. Common brands of 70% alumina containing calcium aluminate cement are ALAMITIS' "calcium aluminate 14" product and Lafarge's Secar 71 product.

The typical average open porosity of the $C_nA_y$ aggregate is 53.5% while the TSG (typical specific gravity) averages 2.9 g/cm$^3$.

Composition Example 5**

| Aggregate | Wt % |
|---|---|
| $C_nA_y$ +10 m | 15% |
| $C_nA_y$ 10/28 m | 30% |
| $C_nA_y$ 28/65 m | 10% |
| $C_nA_y$ −65 m | 11% |
| $C_nA_y$ −325 m | 7% |
| A-2 alumina | 8% |
| A-3000 alumina | 10% |
| A-1000 alumina | 9% |
| STPP (plus addition) | 0.15% |

24% by weight of water was added to give a vibration cast consistency. The material was cast into simple bars in order to determine modulus and crushing strengths. The shape was stripped from the mold in 24 hours and dried at 110° C. Finally, the shape was fired to a temperature of 1100° C. and allowed to reach thermal equilibrium. The shape was allowed to cool and was tested. The results are as follows:
** Example 5 is a calcium aluminate ($C_nA_y$) composition of the instant invention comprising a blend of CA (50% wgt.) and CA$_2$ (50% wgt.).

Apparent porosity=50%
Average pore size=44 microns
Cold crushing strength (ASTM C133)=34.5 MPa
Modulus of Rupture (ASTM C133)=9.3 MPa Example 6

Materials and Methods 6.1 Human MG-63 Cell Culture

MG-63 cells (ATCC, CRL-1427) at passage 88 were cultured in F12 Ham/Minimal Essential Medium (1:1, Gibco) with 10% fetal bovine serum (Gibco, 10082-139) and penicillin streptomycin (Gibco) at 37° C. with 5% CO$_2$ and 90% humidity. Cells were passaged when sub-confluent using trypsin/EDTA (Gibco, 25300-054), and between passages 88-98.

6.2 Human Adult Mesenchymal Stem Cell (hAMSC) Culture

Bone-marrow derived human adult mesenchymal stem cells (Cambrex, PT-2501) were cultured in mesenchymal stem cell growth media (MSCGM, Cambrex, PT-3001, PT-3238) at 37° C. with 5% CO$_2$ and 90% humidity. When sub-confluent, cells were released using trypsin/EDTA and used between passages 3-10. For differentiation, hAMSC were cultured in medium with an osteogenic supplement (Cambrex, PT-3002) containing beta-glycerophosphate, ascorbic acid, and dexamethosone.

6.3 Preparation of Calcium Aluminate Materials

Compositions comprising a calcium aluminate containing phase were obtained from Westmoreland Advanced Materials, LLC (Monessen, Pa., USA). Calcium aluminate of approximately 0.85-2 mm were collected by sieving and sterilized by autoclaving. As used in this patent application, the size of about 0.85 mm to about 2 mm (millimeter) is referred to as a "morsel".

6.4 Seeding of Cells on Calcium Aluminates for Static Culture

One gram of sterile calcium aluminate morsels were placed into each well of a 12-well plate and 1×10$^5$ MG-63 cells or 1×10$^4$ hAMSC were added per well in a total volume of 3-4 mls medium. After 24 hours in culture, the calcium aluminate morsels were washed to remove any unattached cells, transferred to a new well plate, and the medium was replaced.

6.5 Seeding of Cells on Calcium Aluminates for Dynamic Culture

Three-gram samples of sterile calcium aluminates were placed into the bottom of a spinner flask (Bellco Glass, 7761-00100). A total of 2.5×10$^6$ MG-63 cells (ATCC, CRL-1427) at passage 88, or 1.2–1.3×10$^6$ hAMSC were added in a volume of 60 mls of appropriate medium (F12 Ham/Minimal Essential Medium [1:1, Gibco] with 10% fetal bovine serum [Gibco, 10082-139] and penicillin streptomycin [Gibco] at 37 degrees Centigrade with 5% CO$_2$ and 90% humidity) with stirring at 17-20 rpm. After 24 hours in this culture, the calcium aluminate morsels were washed to remove any unattached cells, transferred to new spinner bottles, and the medium was replaced.

6.6 Cell Quantitation by CyQuant Cell Proliferation Assay Kit

Attachment and proliferation of MG-63 cells or hAMSC on calcium aluminates were assessed by the CyQuant assay (Molecular Probes, C-7026). Calcium aluminates samples with cells attached were washed three times with PBS to remove unattached cells, and then stored at −80° C. Samples were subjected to several freeze/thaw cycles, and then assayed as designated by the manufacturer. Each sample is assayed by measuring the fluorescence (480 nm excitation and 500 nm emission) in a Perkin Elmer HTS 7000 Bio Assay Reader. Standard curves were used to convert fluorescence units into cell numbers.

6.7 Viability and Cell Quantitation by Live/Dead Fluorescence Staining

Viability and attachment of cells on the calcium aluminate morsels were assessed with the LIVE/DEAD Viability/Cytotoxicity Assay kit (Molecular Probes, L-3224). Calcium aluminate samples with cells attached were washed three times with PBS and then stained with the Live/Dead fluorescent dye as suggested by the manufacturer. The Live/Dead stained samples were viewed using a fluorescent microscope (Nikon Eclipse E600), and viability was determined. Ten morsels of calcium aluminate were chosen at random and the live and dead cells were counted.

6.8 Cell Attachment and Morphology by Scanning Electron Microscopy

Calcium aluminate samples of the present invention were washed three times with phosphate-buffered saline (PBS) and fixed in 2.5% gluteraldehyde in PBS. The samples were washed with PBS, stained with osmium tetroxide, washed with water, dehydrated through an ethanol series, and critical point dried. Samples were mounted, gold-coated, and viewed with a Hitachi 2460 scanning electron microscope at an accelerating voltage of 5 kV or 15 kV. Digital images were captured at varying magnifications.

6.9 Alkaline Phosphatase Histochemical Staining

Reagents were prepared using the alkaline phosphatase histochemical staining kit (Sigma 85-4C). Samples were washed three times with PBS, fixed for one minute with citrate-buffered methanol, washed three times with distilled water, and stained as described by the manufacturer.

6.10 Alkaline Phosphatase Biochemical

Samples were washed three times with PBS and stored at $-80°$ C. To prepare lysates, samples were subjected to a series of freeze/thaw cycles and vortexed. Lysates were clarified by centrifuge in a microfuge (12,000×g for 10 seconds) and the supernatant was assayed in triplicate for alkaline phosphatase activity. The buffer solution was prepared by mixing equal volumes of 2-amino-2-methyl-1-propanol (Sigma A9879), p-nitrophenol phosphate (Sigma 104-0), and 1M $MgCl_2$. A standard curve of p-nitrophenol was used to estimate p-nitrophenol produced. Alkaline phosphatase activity was calculated as pmol p-nitrophenol produced per microgram of protein in cell lysate per hour. Absorbances were read at 405 nm on a BioRad Model 3550 Microplate Reader. Protein concentration was estimated using the BCA Protein Assay (Pierce Biotechnology, 23225) using bovine serum albumin to generate standard curves.

6.9 Chick Chorioallantoic Membrane (CAM) Assay

Fertilized White Leghorn chicken eggs were incubated for three days at 100° F. and 70% relative humidity. The eggs were cracked into 100 mm×20 mm sterile cell culture dishes containing 4 mL of sterile Dulbecco's Modified Eagle Media (InVitrogen) with 1.5 g/L sodium bicarbonate. Embryos were incubated at 38° C. for an additional 7 days to allow for the CAM to fully develop. Morsels of calcium aluminate were applied to CAMs at day 10 and incubated for 72 hrs. Immediately prior to imaging, the vasculature was labeled with Qdots by injection of 10-μl 2-8 mM Qdots into the large vitelline vein using glass needles with ~100 μm diameter bore. Light and fluorescence imaging to measure angiogenic response was performed immediately post injection using an inverted Zeiss Axiovert 135TV microscope equipped with a Hamamatsu ORCA II cooled CCD camera. Fluorescence images of quantum dots were acquired with a 450/50 nm excitation filter and appropriately selected 20 nm wide bandpass emission filters, centered on the emission maxima of the quantum dots.

6.10 Statistical Analysis

The Vassar Stats online statistical program (http://faculty.vassar.edu/lowry/VassarStats.html) was used to calculate means, standard errors, analysis of variance (ANOVA), Tukey's post hoc tests, and t-tests. ANOVA and the Tukey post hoc test were used to compare multiple means. Statistical significance was $p<0.05$.

Results

MG-63 Cells Attach on Calcium Aluminates Proliferate, and Maintain High Viability Under Dynamic and Static Seeding and Culture Conditions.

Figure 1B:
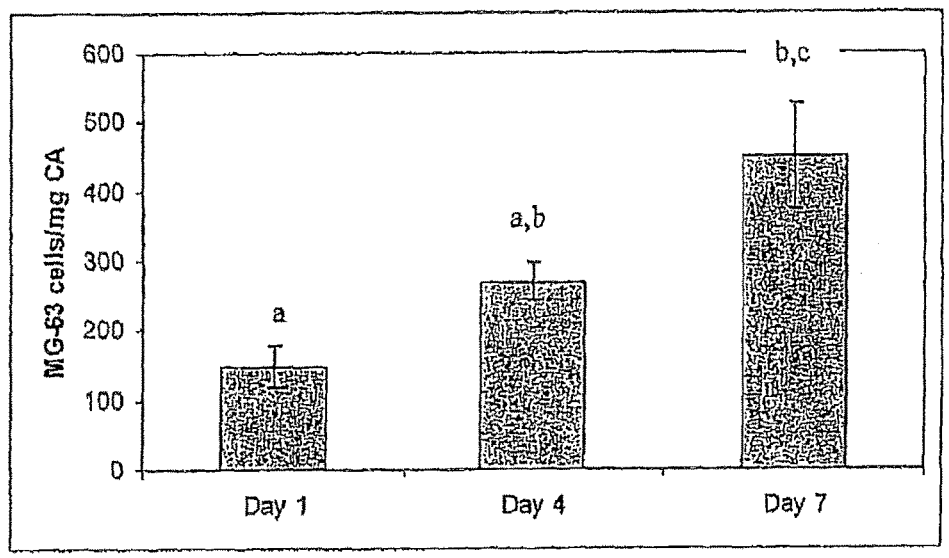
Figures 2A, 2B:
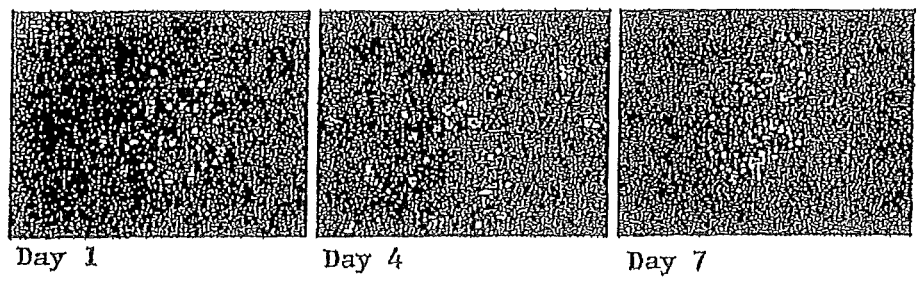
FIG. 2. MG-63 cells maintain high viability when seeded and cultured on compositions comprising a calcium aluminate containing phase of the present invention.
Figure 3:
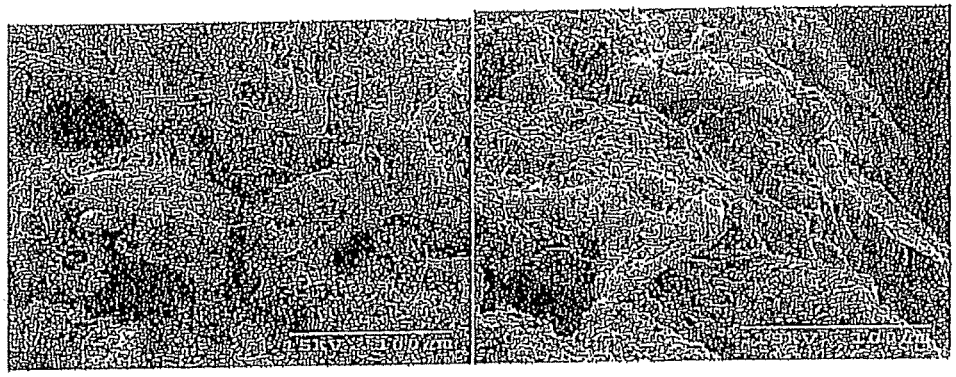
FIG. 3. MG-63 cells attach on compositions comprising a calcium aluminate containing phase of the present invention as assessed by scanning electron microscopy.

To assess the attachment and proliferation of MG-63 cells on calcium aluminates of the present invention under dynamic culture conditions, a fixed amount of calcium aluminate (3.0 g per flask) was incubated in spinner flasks with $2.5 \times 10^6$ MG-63 cells. For static conditions, a fixed amount of calcium aluminate (1.0 g per well) was incubated in a 12-well plate with $1.1 \times 10^5$ MG-63 cells per well. The CyQuant assay was used to determine attachment and proliferation of MG-63 cells on the calcium aluminate at days 1, 4, and 7. Samples taken on day 1 represent initial MG-63 cell attachment on the calcium aluminate. Samples were then washed to remove unattached cells after day 1, and assayed on days 4 and 7 of culture to assess proliferation. Under dynamic culture conditions, cell numbers increased over the one-week period as assessed by CyQuant assay with a statistically significant increase ($p<0.05$) between days 1 and 7 determined by ANOVA and Tukey's post hoc test (FIG. 1A). This statistically significant increase was observed in four independent experiments. Under static culture conditions, there was a statistically significant increase ($p<0.05$) consistently observed in three independent experiments between days 1 and 7, and days 4 and 7 as determined by ANOVA and Tukey's post hoc test (FIG. 1B). Throughout the one week period examined, the viability of MG-63 cells under dynamic or static culture conditions is 90% or higher, as assessed by Live/Dead fluorescent staining (FIG. 2). Scanning electron microscopy showed that MG-63 cells produce an extracellular matrix, attach, and spread over the surface of the calcium aluminate (FIG. 3).

Human Adult Mesenchymal Stem Cells (hAMSC) Attach on Calcium Aluminates and Show Variability in Proliferation Under Static and Dynamic Culture Conditions.

Figure 4A:
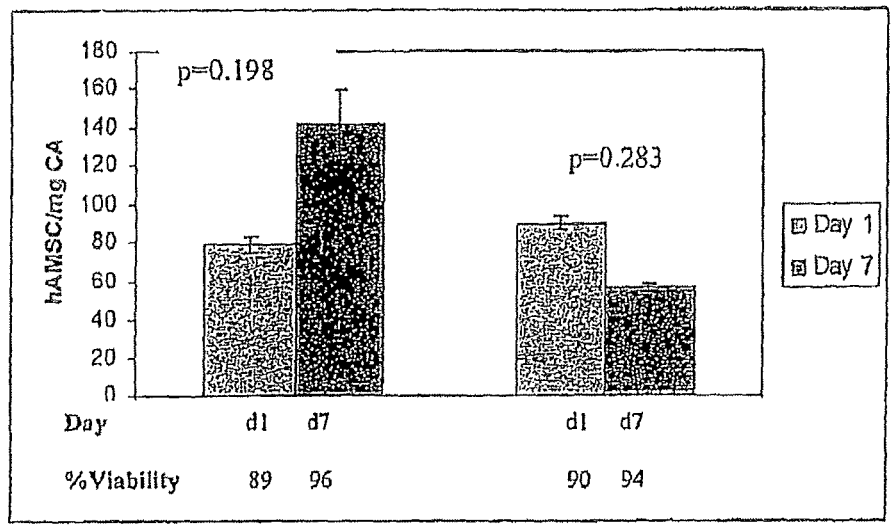
FIG. 4. Human adult mesenchymal stem cells attach and show high viability but variable proliferation on compositions comprising a calcium aluminate containing phase of the present invention under static (A) and dynamic (B) culture conditions.
Figure 4B:
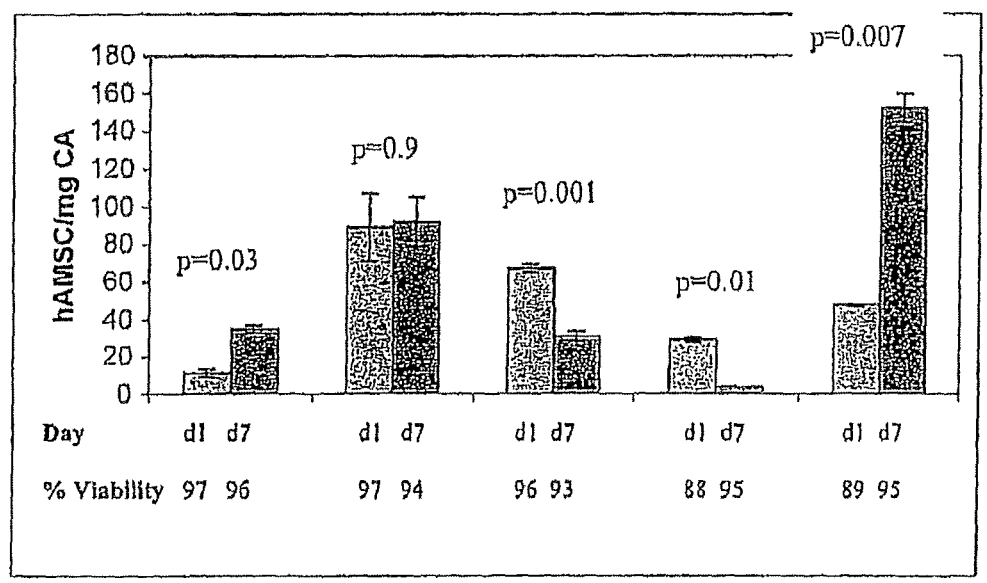
Figure 5:
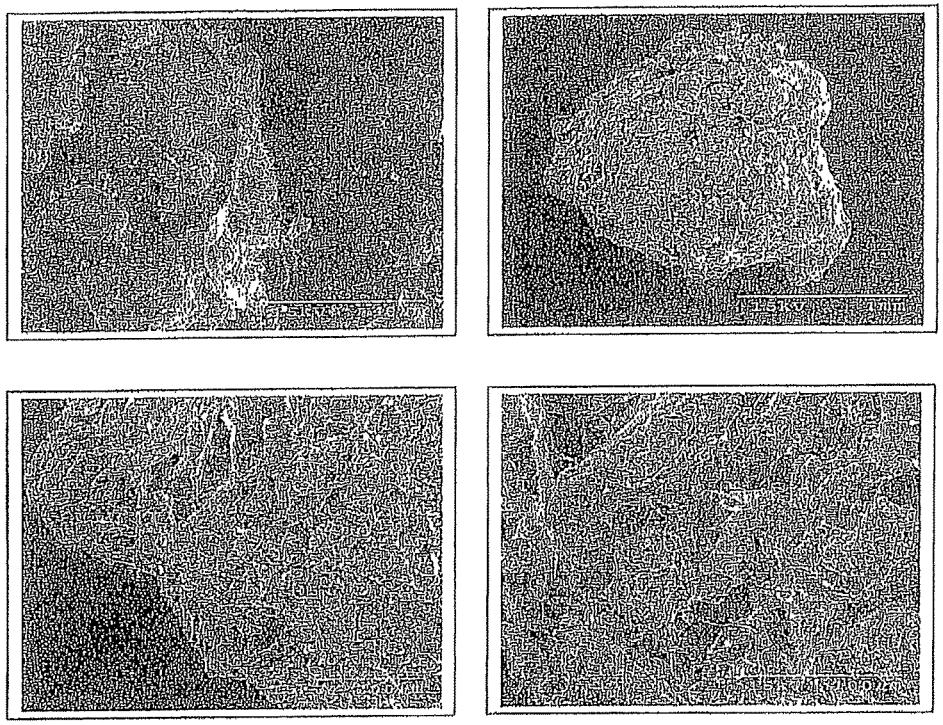
FIG. 5. Human adult mesenchymal stem cells attach on compositions comprising a calcium aluminate containing phase of the present invention as assessed by scanning electron microscopy.

To assess the attachment and proliferation of hAMSC on calcium aluminate, a fixed amount of calcium aluminate (1.0 g per well for static cultures; 3.0 g/spinner bottle for dynamic cultures) was seeded with human adult mesenchymal stem cells ($1 \times 10^4$ cells per well for static cultures; $1.2 \times 10^6$ cells per spinner flask for dynamic cultures). Samples taken and assayed by the CyQuant assay on day 1 represent initial hAMSC attachment on the calcium aluminate. Samples were then washed to remove unattached cells after day 1, and assayed by CyQuant on days 4 and 7 of culture to assess proliferation. Human adult mesenchymal stem cells are able to attach to calcium aluminate after 24 hours in static or dynamic culture as assessed by the CyQuant assay. FIG. 4 presents the results of two independent and representative experiments under static culture conditions (FIG. 4A) and five independent experiments under dynamic conditions (FIG. 4B). There was variability in the proliferation of hAMSC among the experiments under static and dynamic culture conditions. In some cases there was a statistically significant increase in cell numbers over the seven day culture period, in some cases there was a statistically significant decrease, and in some cases there was no difference. In all of the experiments, those cells attached to the calcium aluminate maintained viability over 90% under either static or dynamic culture (FIGS. 4A and B). Scanning electron microscopy of hAMSC cultured on the calcium aluminate through three weeks of culture show cell attachment, though the cells do not appear to be as spread over the surface as is typical for these cells on tissue culture plastic (FIG. 5).

Differentiation of Human Adult Mesenchymal Stem Cells on Calcium Aluminates

Figures 6A, 6B:
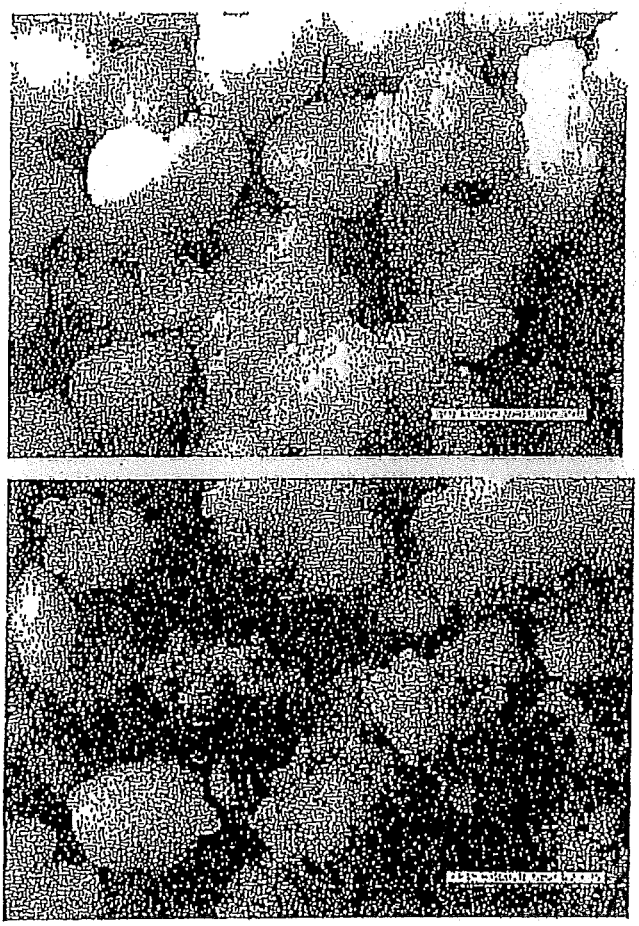
FIG. 6. hAMSC on CA express alkaline phosphatase in response to an osteogenic supplement.

To assess the differentiation of human adult mesenchymal stem cells into osteoblasts, hAMSC attached to the calcium aluminate were cultured for 14 days in medium with an osteogenic supplement (Cambrex, PT-3002) containing beta-glycerophosphate, ascorbic acid, and dexamethasone or in control medium. Bone-marrow derived human adult mesenchymal stem cells (Cambrex, PT-2501) were cultured in mesenchymal stem cell growth media (MSCGM, Cambrex, PT-30001, PT-3238) at 37 degrees Centigrade (C) with 5% CO2 and 90% humidity. When sub-confluent, the cells were released using trypsin/EDTA and used between passages 3 to 10. The levels of induced alkaline phosphatase under both conditions were assessed biochemically and histochemically (FIGS. 6A and B, respectively). Based on three independent experiments, hAMSC on the calcium aluminate cultured with osteogenic supplement-containing medium show a statistically significant increase (p=0.04) in alkaline phosphatase biochemical activity relative to controls, consistent with osteoblast differentiation. Histochemical staining for alkaline phosphatase (FIG. 6B) confirms the results from the biochemical assay: alkaline phosphatase staining is readily detected on numerous morsels in the OS-treated samples, and little staining is detected in the controls, even though cells were present on the control samples as detected by Live/Dead staining (data not shown).

Figure 7:
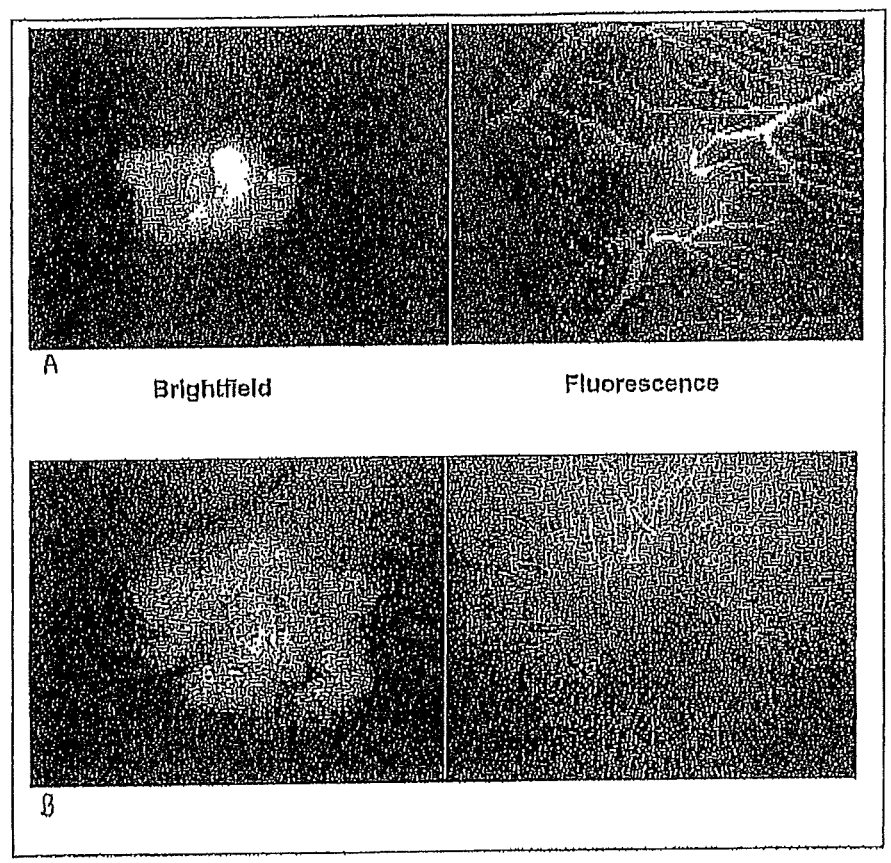
FIG. 7. Compositions comprising a calcium aluminate containing phase of the present invention is non-toxic as assessed by chick CAM assays.

Calcium Aluminate is Non-Toxic In Vivo as Assessed by Chick Chorioallantoic Membrane (CAM) Assays To assess calcium aluminate toxicity using an in vivo assay, we employed the chick embryonic chorioallantoic membrane assay (REFS). Morsels of the calcium aluminate, or clinically relevant calcium phosphate materials (ChronOS) as controls, were placed on chick CAMs and the formation of blood vessels in the vicinity of the calcium aluminate implant was assessed by fluorescent microscopy. FIG. 7 shows that calcium aluminate has no obvious negative effect on the vascularization of the chick CAM. Toxic and negative effects could be evidenced in the embryo's death, the material causing severe inflammation, or neighboring blood vessels regression/death. None of these appeared to have occurred.

Figure Legends

FIG. 1. MG-63 cells attach and proliferate on calcium aluminates under static (A) and dynamic (B) culture conditions as assessed by CyQuant assay. For dynamic culture, a fixed amount of calcium aluminate (3.0 g per flask) was incubated in spinner flasks with $2.5 \times 10^6$ MG-63 cells. For static culture, a fixed amount of calcium aluminate (1.0 g per well) was incubated in a 12-well plate with $1.1 \times 10^5$ MG-63 cells per well. The CyQuant assay was used to determine attachment and proliferation of MG-63 cells on calcium aluminate at days 1, 4, and 7. Samples taken on day 1 represent initial MG-63 cell attachment on calcium aluminate. Samples were washed to remove unattached cells after day 1, and assayed on days 4 and 7 of culture to assess proliferation. For static culture (A), each bar represents the mean and standard error of the mean of three wells from a representative experiment. Three independent experiments were performed. There is a statistically significant increase in MG-63 cell numbers between days 1 and day 7 ($p<0.01$), and days 4 and 7 ($p<0.05$) determined by ANOVA and Tukey post-hoc tests, consistent with proliferation. This statistically significant difference was in common among the three independent experiments. For dynamic culture (B), each bar represents the mean and standard error of the mean of three samples taken from the spinner flask at each time point from a representative experiment. Four independent experiments were performed. There is a statistically significant increase in MG-63 cell numbers between days 1 and day 7 ($p<0.05$) determined by ANOVA and Tukey post-hoc tests, consistent with proliferation. This statistically significant difference was in common among all four independent experiments.

FIG. 2. MG-63 cells maintain high viability when seeded and cultured on calcium aluminates. MG-63 cells seeded and cultured on calcium aluminates over a period of seven days under static and dynamic conditions were assessed for viability by Live/Dead staining. Fluorescent micrographs (A) are representative of a dynamic culture on days 1, 4, and 7. Data in B are the means and standard errors of the mean of percent viabilities of four independent experiments. For each independent experiment, live and dead cells on ten pieces of calcium aluminate were counted under fluorescent microscopy from each of three wells (static) or three samples (dynamic).

FIG. 3. MG-63 cells attach on calcium aluminates as assessed by scanning electron microscopy. MG-63 cells cultured under static conditions for four days were observed by scanning electron microscopy.

FIG. 4. Human adult mesenchymal stem cells attach and show high viability but variable proliferation on calcium aluminates under static (A) and dynamic (B) culture conditions. For static culture, a fixed amount of calcium aluminate (1.0 g per well) was seeded with human adult mesenchymal stem cells ($1 \times 10^4$ cells per well) in 12-well plates. For dynamic culture, a fixed amount of calcium aluminate (3.0 g/spinner bottle) was seeded with $1.2 \times 10^6$ hAMSC per spinner flask. Samples were taken and assayed by the CyQuant assay on day 1 represent to assess initial hAMSC attachment on calcium aluminate. Calcium aluminate morsels were then washed to remove unattached cells after day 1, and assayed by CyQuant on day 1 and day 7 of culture to assess attachment and proliferation. For static cultures (A), the results of two independent and representative experiments (1-4) are shown. Each bar represents the mean and standard error of the mean of three wells. For dynamic cultures (B), the results of five independent experiments (1-6) are shown. Each bar represents the mean and standard error of the mean of three replicate samples from each a spinner flask. A two-tailed t test was used to assess statistically significant differences between means, and the p-values are shown above each independent experiment on the graph. The viability of attached cells as assessed by Live/Dead staining on each day for each experiment is also shown. For each independent experiment, live and dead cells on ten pieces of calcium aluminate were counted under fluorescent microscopy from each of three wells per 12-well plate (static, A) or three samples per spinner flask (dynamic, B).

FIG. 5. Human adult mesenchymal stem cells attach on calcium aluminates as assessed by scanning electron microscopy. hAMSC cultured under dynamic conditions for 7 days (left) and 21 days (right) were observed by scanning electron microscopy.

FIG. 6. hAMSC on calcium aluminate express alkaline phosphatase in response to an osteogenic supplement. hAMSC attached to calcium aluminate were cultured for 14 days in medium with an osteogenic supplement (OS+, containing beta-glycerophosphate, ascorbic acid, and dexamethasone) or in control medium. The levels of induced alkaline phosphatase under both conditions were assessed biochemically (A) and histochemically (B). The biochemical data are the mean and standard error of the mean of three independent experiments. There is a statistically significant increase (p=0.04) in alkaline phosphatase biochemical activity in OS-treated cells relative to controls, thereby consistent with osteoblast differentiation. Histochemical staining for alkaline phosphatase (B) shows that alkaline phosphatase staining is readily detected on numerous morsels in the OS-treated samples, and little staining is detected in the controls, even though cells were present on the control samples as detected by Live/Dead staining (data not shown). Scale bar=1.25 mm.

FIG. 7. Calcium aluminate is non-toxic as assessed by chick CAM assays. Morsels of calcium aluminate (A) and ChronOs (control, B) were placed on the chorioallantoic membrane of embryonic chicks. One day later the embryos were injected with 8 microM 705 nm emission Qdots that were conjugated with 2000 MW PEG. Brightfield (left) and fluorescent (right) images were captured and show that the developing vasculature around the CA shows no indication of inhibition/toxicity.

As will be appreciated by those persons skilled in the art, this study (Examples 6-9) assessed the calcium aluminates of the present invention to determine their ability to support cell growth in static and dynamic culture conditions. After calcium aluminates were assessed through in-vitro studies, we conducted in-vivo studies through the CAM assay to determine the biocompatibility of calcium aluminate. Calcium aluminates were chosen due to their advantages when compared to other synthetic materials. Most forms of calcium aluminate will hydrate and form a bonding matrix. As a result, a three dimensional structure can easily be created that will exhibit high strengths (high degree of tensile stress and compressive stress resistance) without the need for thermal treatment, such as with calcium phosphates, for example but not limited to calcium orthophosphate, which are more brittle, difficult, and expensive to manufacture. In addition to providing a physically superior bond mechanism, hydrated calcium aluminate is easily metabolized by the body and overtime is replaced with natural bone. If desired, calcium aluminate can be treated so that it will not hydrate and thus will remain as a permanent support structure. Another advantage of calcium aluminate is that by carefully choosing the ratio of reactants to form calcium aluminate, the type of calcium aluminate formed can be controlled along with the resulting porosity, surface structure, and solubility of the material. As mentioned briefly, this may allow a degree of cell attachment control as this potentially relates to surface structure. By choosing the ratio of reactants to form calcium aluminate the type of calcium aluminate that forms can be controlled, along with the resulting porosity and solubility of the material.

Some synthetic materials, such as the forms of calcium aluminates, which we have investigated, have a natural porosity due to their synthetic mechanism. This permits the necessary vascularization and hence bond between the implant and natural bone. In addition, the hardness of the CA material and natural bone are very similar and therefore abrasion loss is drastically reduced. Therefore, synthetic ceramics such as calcium aluminate should be able to replace metal implants and be more advantageous to long term and stable medical implants and the industry supporting this technology.

Calcium aluminates are composed of hydratable compounds that add strength to the material via a dissolution/precipitation reaction when mixed with water. Porosity is able to be controlled and the material can be molded into any desirable shape. Calcium aluminate can be engineered to match the desired finished structure, and, in addition, in the form of hydrates, these materials will slowly be metabolized by the body. There is limited research available on calcium aluminates for use in tissue engineering. From the limited research, there have been few in-vivo studies. However, Klawitter and Hulbert were able to determine that calcium aluminates do not cause an inflammatory response when implanted into dog femurs.

In this study (examples 6-9) we have shown that calcium aluminate material of the present invention are able to support the growth and high viability of two types of cells; the human adult mesenchymal stem cells and MG-63 osteosarcoma cells. MG-63 cells attach and proliferate in dynamic and static culture conditions over the course of 7 days. The MG-63 cells also maintain high viability at or above 90% during the 7 days in both types of culture. Human adult mesenchymal stem cells (hAMSC) attach in dynamic and static culture conditions. The hAMSC maintain high viability at or above 90% throughout 7 days in both cultures. Proliferation is variable with the hAMSC in both culture conditions. Another possible reason for the observed variation may have been due to the inconsistency of hAMSC, which were purchased at different times thereby resulting in different demographic characteristics based on the source of the human adult mesenchymal stem cells. However, even with the variability with the hAMSC proliferating on calcium aluminate, the cells are able to differentiate into osteoblasts and express alkaline phosphatase activity.

Furthermore, we have assessed the biocompatibility of calcium aluminates through in-vivo chick chorioallantoic membrane (CAM) assays. We have determined that the calcium aluminate compositions of the present invention do not cause a toxic response to the chick membranes, which is consistent with our in-vitro results. Based on the in-vitro studies involving the attachment and proliferation of human adult mesenchymal stem cells and MG-63 cells, in-vitro differentiation studies of hAMSC, and the in-vivo CAM assays, we believe calcium aluminate materials may be an effective material for bone regenerative medicine.

Example 7

Figure 24:
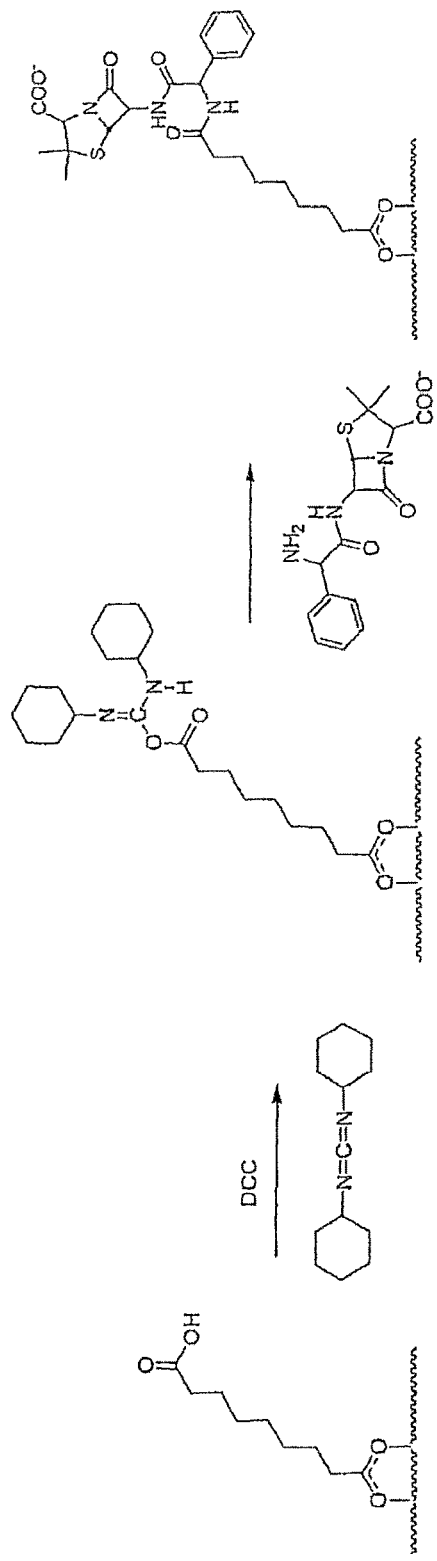
FIG. 24 shows the functionalization (coupling) for bonding an antibiotic, namely ampicillin, to a calcium aluminate containing composition of this invention.
Figure 25:
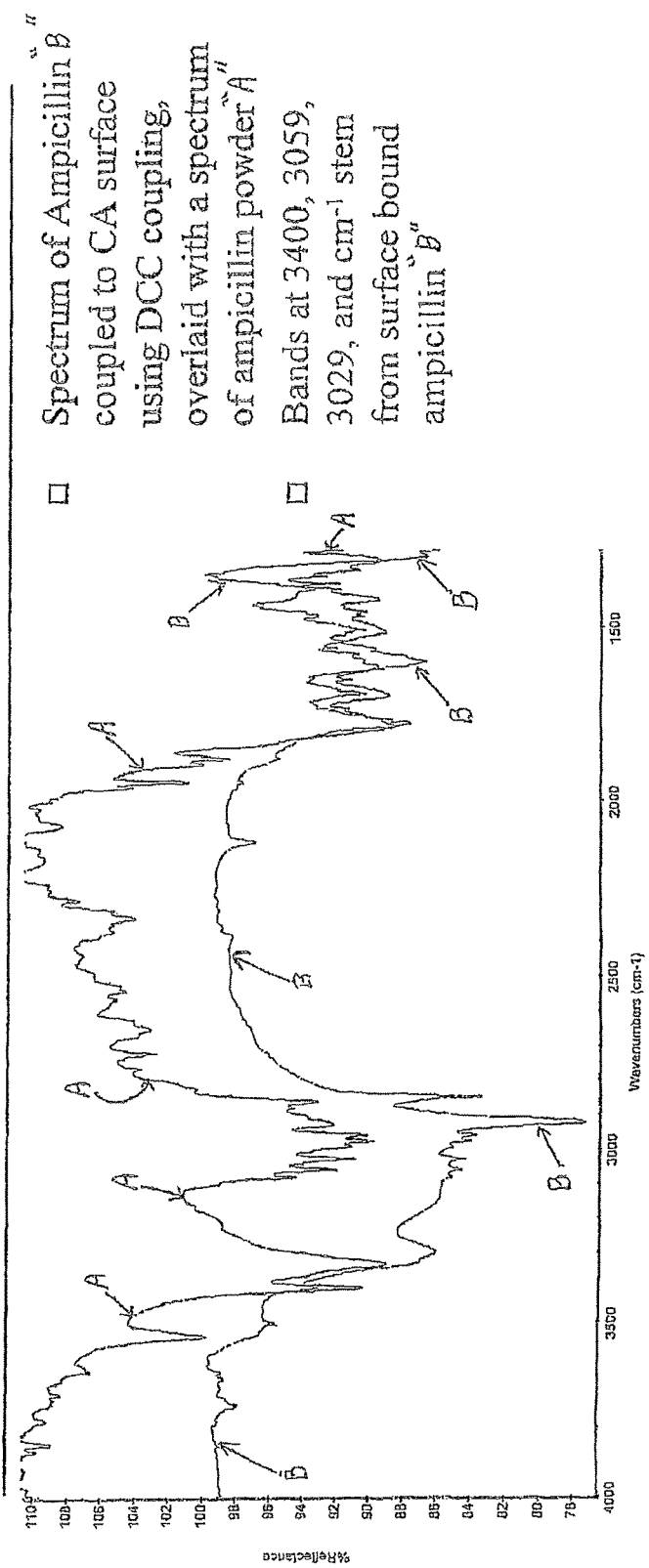
FIG. 25 shows the spectra of an antibiotic, namely ampicillin, linked to a dicarboxylic-functionalized calcium aluminate containing composition of this invention.

The following procedures were followed to functionalize the ceramic body and/or the calcium aluminate compositions of the present invention. As used herein the terms "functionalize" and/or "functionalization" refer(s) to the modification of the ceramic body and/or the compositions comprising a calcium aluminate containing phase as described herein of this invention by the deposition or attachment of an organic acid, a phosphonic acid, an amine, or N,N-dicyclohexylcarbodiimide to the ceramic body and/or the calcium aluminate containing phase of the compositions of this invention. The functionalization forms a functionalized interface between the ceramic body or the calcium aluminate containing phase of the compositions of this invention and the biological tissue which results in an improvement of the ceramic body's or the calcium aluminate containing composition's biocompatibility and/or resistance to infection. FIGS. 19-26 show examples of the functionalization of the ceramic body and/or calcium aluminate containing compositions of the present invention with, such as for example but not limited to, organic acids, phosphonic acid, an amine, and N,N-dicyclohexylcarbodiimide. FIG. 24 shows the coupling chemistry for the attachment of an antibiotic to the ceramic body and/or calcium aluminate containing compositions of this invention. FIG. 26 shows the coupling of a peptide sequence to an amino-functionalized calcium aluminate containing composition of this invention wherein calcium aluminate was functionalized with 12-aminododecanoic acid and subsequently reacted with 3-maleimidopropionic acid N-hydroxysuccinimide ester (NHS) as linking agents (coupling agents). The morsels of calcium aluminate containing compositions set forth in the following functionalization (deposition) examples were obtained from Westmoreland Advanced Materials Bioceramics, Inc. (Monessen, Pa., USA). The composition of the calcium aluminate that was employed for the deposition and attachment examples set forth below was primarily a CA (50% by weight) and $CA_2$ (50% by weight) composition of the present invention. It will be understood by those skilled in the art that any of the compositions comprising a calcium aluminate containing phase of this invention as described herein may be employed as the composition for attaching the linker and any desired chemical and biologic moiety. The CA and $CA_2$ composition was chosen merely as an example and is not to be construed to limit the scope of the present invention. It is important to note that when the linker group is an acid the head group and the tail group of the acid molecule may be varied to have varying functionalities in order that the ceramic body or the calcium aluminate containing compositions being modified provide one or more reactive locations for the attachment of other chemical molecules or biological moieties.

7.1 Octadecylphosphonic Acid Deposition 1 mM solution of octadecylphosphonic acid was prepared in dry THF (tetrahydrofuran). Morsels of calcium aluminate compositions of this invention were placed into this solution at room temperature. After remaining in the solution for one hour the calcium aluminate compositions were removed from the solution and placed in a glass dish and dried in the oven at 120° C. overnight, approximately 12 hours.

7.2 Stearic Acid (Octadecanoic Acid) Deposition 1 mM solution of stearic acid was prepared in dry distilled THF. Morsels of calcium aluminate containing compositions of this invention were placed in this solution for 1 hour at room temperature. The calcium aluminate containing compositions were then removed from the solution and placed in a 120° C. for 12 hours to dry.

7.3 12-Bromododecanoic Acid Deposition

Morsels of CA containing compositions of this invention were placed in a 2 mM solution of 12-bromododecanoic acid in THF for 1 hour at room temperature. The calcium aluminate containing compositions were removed from solution and dried in the oven at 120° C. for 12 hours.

7.4 12-Aminododecanoic Acid Deposition

A small amount of 12-aminododecanoic powder was placed in dry THF and sonicated for 5 minutes to form a saturated solution. Morsels of calcium aluminate containing compositions of this invention were dipped in the saturated 12-aminododecanoic acid solution for 1 hour at room temperature. The calcium aluminate containing compositions were removed from solution and placed in oven at 120° C. for 12 hours.

7.5 1,12-Dodecanedicarboxylic Acid Deposition

Morsels of calcium aluminate containing compositions of this invention were dipped in a 1 mM solution of 1,12-dodecanedicarboxylic acid for 1 hour at room temperature. The calcium aluminate containing compositions were then removed from solution and dried in the oven for 12 hours at 120° C.

7.6 DCC/NHS Linking

Morsels of calcium aluminate containing compositions of this invention that have been functionalized with 1,12-dicarboxylic acid were placed in a solution of 2 mM N-hydroxysuccinimide and 2 mM N,N-dicyclohexylcarbodiimide (DCC) for 24 hours. The calcium aluminate containing compositions were removed from solution and placed under vacuum on a schlenk line (0.1 torr) for 1.5 hours to dry.

7.7 Ampicillin or Vancomycin Attachment.

Morsels of calcium aluminate containing compositions of this invention that had been functionalized with the NHS linker were dipped in 1 mg/ml solutions of either ampicillin or vancomycin in methanol immediately after removal from vacuum tube. The calcium aluminate containing compositions were left in solution for 24 hours at 30° C. The calcium aluminate containing compositions were then removed from solution and dried under vacuum in a vacuum tube on a schlenk line (0.1 torr).

7.8 RGDC and KRSR Peptide Linking

Morsels of calcium aluminate containing compositions of this invention that had been functionalized with 12-aminododecanoic acid were dipped in a solution of 1 mM 3-maleimidopropionic acid N-hydroxysuccinimide ester (NHS) in acetonitrile for 24 hours at room temperature. The calcium aluminate containing compositions were then removed from solution and placed under vacuum for 24 hours to dry. The calcium aluminate containing compositions were then dipped in 1 mg/ml aqueous solution of either RGDC peptide (arginine-glycine-aspartate-cysteine) or KRSR peptide (lysine-arginine-serine-arginine) for 24 hours. The calcium aluminate containing compositions were again removed from solution and placed under vacuum (0.1 torr) for 24 hours.

Example 8

In this example, modified calcium aluminate morsels described in example 7.2 were taken to form a cast shape. Modified morsels of the appropriate size distribution (set forth below) were blended with −325 mesh calcium aluminate to form a composition. The size distribution of this composition was 50% (wt) −325 mesh, 25% (wt) −10+60 mesh and 25% (wt) −60 mesh. To this composition 20% (wt) water was added to form a vibratable castable which was formed into a 1×1×5" bar using a Teflon coated mold. The composition was allowed to set and then cured for 24 hours. It was then analyzed to determine that the stearic acid linker modification was still intact, which it was. This example is a basis for a prosthetic device formed of the functionalized calcium aluminate where the modification is throughout the prosthetic and is available as the prosthetic is metabolized. This strategy allows the applicants of the present invention to modify the calcium aluminate morsels with different functional groups thereby giving the present applicants the ability to target two or more biological and/or chemical processes.

Example 9

In this example calcium aluminate morsels were blended to provide the appropriate size distribution (set forth below) for a vibration castable. The size distribution of this composition was 50% (wt) −325 mesh, 25% (wt) −10+60 mesh and 25% (wt) −60 mesh. To this composition 25% (wt) water was added to form a vibratable castable which was formed into a 1×1×5" bar using a Teflon coated mold. The composition was allowed to set and then cured for 24 hours. This entire shape was then treated according to example 7.2 in order to functionalize the surface and near surface (due to porosity) of the bar. The bar was analyzed to determine successful stearic acid functionalization. This was the case. This example is the basis for a prosthetic device formed of the functionalized calcium aluminate of the present invention where the modification would be only on the surface or near surface of the prosthetic. Addition of an antibiotic functional group, as described herein, allows for the potential attack of the formation of biofilms on the surface of the prosthetic device. The present modification may be used as a barrier to tissue attachment to treat the inside of a skull plate or implant to successfully prevent tissue attachment to the inside of the skull.

Example 10

Tricalcium Orthophosphate+Vancomycin

The scaffolding material is $Ca_3(PO_4)_2$ in the form of a dry particles (morsels) of the size 100% minus 30 mesh (i.e. all particles sized smaller than 30 mesh). The $Ca_3(PO_4)_2$ dry particles or morsels were treated in the same chemical manner as described in Examples 7.1 to 7.6, hereinabove, however, in this Example 10 the $Ca_3(PO_4)_2$ morsels were substituted for the CA and the attachment was performed on the non aggregated (i.e. not bonded together in a monolithic form) scaffold material $Ca_3(PO_4)_2$. In this Example 10, the morsels of non aggregated $Ca_3(PO_4)_2$ were treated according to the chemical pathway listed in Example 7.7, hereinabove, resulting in a linked vancomycin and $Ca_3(PO_4)_2$ morsels (i.e. a functionalized composition of a calcium orthophosphate and attached antibiotic of vancomycin). The resulting functionalized composition has the characteristic of a plastic consistency such that the functionalized composition is mechanically pliable by the use of the human hand and adheres to natural bone where it sets (becomes hardened in place) providing mechanical support and bonding of the encompassed bone.

Example 11A

Dicalcium Orthophosphate+BMP2

The scaffolding material is $Ca_2(HPO_4)_2$ which was mixed with water (in the amount of from five to fifty percent by weight based on the fines of the dicalcium orthophosphate composition) and heat treated according to the literature known by those person skilled in the art (treated at 1000 degrees Centigrade for 24 hours) resulting in the formation of a monolithic shape with a composition of $Ca_2(HPO_4)_2$ and hydroxyapatite. This monolith was then treated according to the chemical pathway listed in Example 7.5, hereinabove. however in this Example 11 the $Ca_2(HPO_4)_2$ was substituted for the calcium aluminate. After this the samples were placed in a solution of 10 ug/ml BMP-2 (human source: *E. coli*, MW 26, 018, 95% purity and human source; a Chinese hamster ovary cell line, purity 95%). The material was left in solution for 24 hours at 30° C. (centigrade). After which the material was removed and dried under vacuum. Attachment of BMP-2 to both $Ca_2(HPO_4)_2$ and hydroxyapatite occurred. It will be appreciated that mixing CaP with water and employing heat treatment of the CaP forms a monolithic structure. The resulting functionalized composition has the characteristic of a plastic consistency such that the functionalized composition is mechanically pliable by the use of the human hand and adheres to natural bone where it sets (becomes hardened in place) providing mechanical support and bonding of the encompassed bone.

Example 11B

CaP+BMP2

Figure 30:
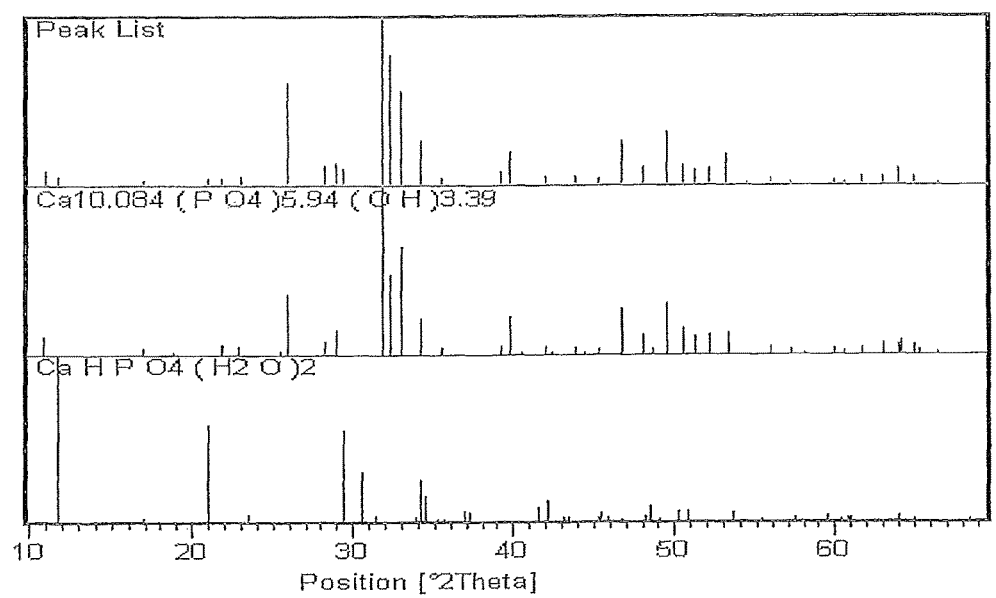
FIG. 30 is a graph that shows the multiphase nature of CaP (calcium phosphate) as analyzed using PXRD (powder x-ray diffraction) and was scanned from 5 to 70°2θ at 720.090 seconds per step and scan speed of 0.002947 degrees/second.

Calcium phosphate (CaP) was cast into thin discs using a commercially available hydroxyapatite ($(Ca_5(PO_4)_3OH)$; HA) powder (Sigma-Aldrich) and a silicon mold in the following manner. HA was ground to a fine particle size using a mortar and pestle. The powder was mixed with 25 mmol phosphoric acid in a 1.000 g:1.60 mL ratio. The resulting slurry was placed into silicon molds and dried at room temperature for a 24 hour period. Following this period, discs were removed from the mold and heat treated at 1000° C. for a period of 4 hours. The heat-treated discs were analyzed by Powder X-Ray Diffraction (PXRD). Ninety-five percent of the sample is composed of hydroxyapatite, the remaining 5% is $CaHPO_4(H_2O_2)_2$. FIG. 30 shows a graph of Powder X-Ray Diffraction results of a CaP of the present invention.

Figure 31:
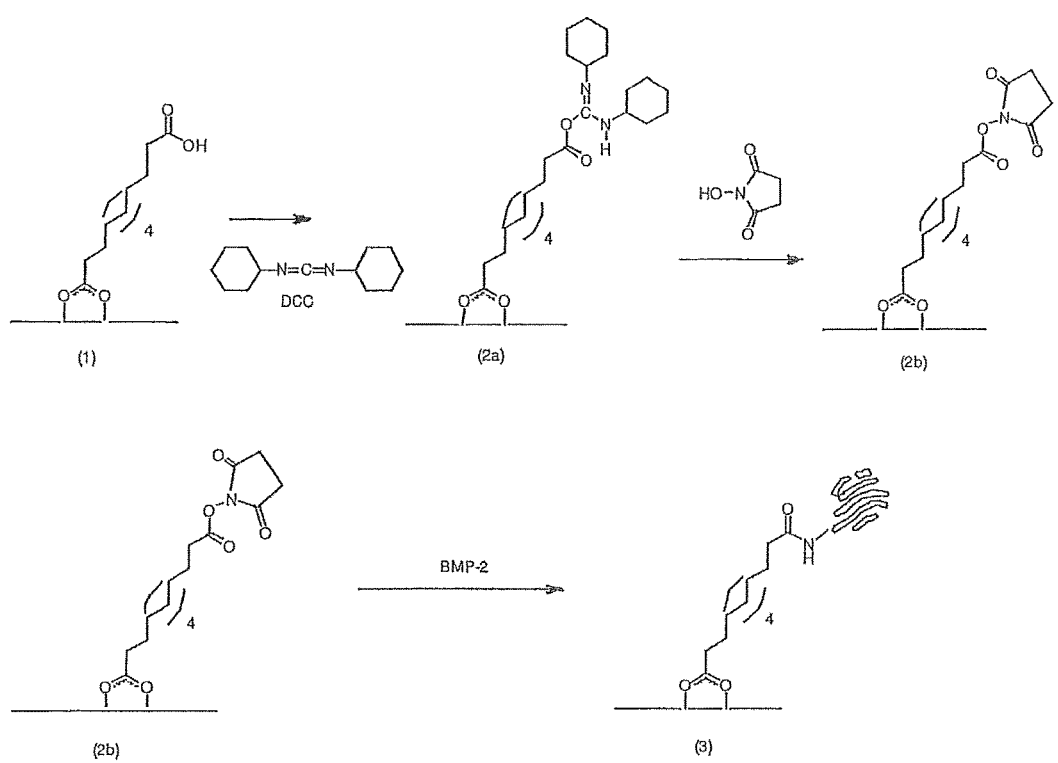
FIG. 31 shows a schematic representation of BMP-2 (bone morphogenic protein 2) attachment to CA.

The protein, bone morphogenic protein 2 (BMP-2) was immobilized on the surface of CaP via a 3-step linker system. First, a 1 mM 1,12-dodecanedicarboxylic acid solution was prepared in distilled THF. CaP discs were submerged in the solution for 1 hour at room temperature. CaP was then dried at 120 degrees Celsius for 24 hours. Following confirmation of 1 mM 1,12-dodecanedicarboxylic acid adsorption onto the CaP surface using DRIFT spectroscopy, CaP disks were submerged in a 2 mM dicyclohexylcarbodiimide NHS ester solution in THF for 24 hours at room temperature. CaP disks were then stored at 0.1 Torr for 24 hours. Finally, BMP-2 was covalently attached to the linker by submerging CaP discs in a 10 ppm BMP-2/ddH2O solution for 24 hours at 4 degrees Celsius. The peptide linkage was confirmed using DRIFT spectroscopy. FIG. 31 shows a schematic representation of bone morphogenetic protein-2 attachment.

The resulting functionalized composition has the characteristic of a plastic consistency such that the functionalized composition is mechanically pliable by the use of the human hand and adheres to natural bone where it sets (becomes hardened in place) providing mechanical support and bonding of the encompassed bone.

Example 12

CA+CaP+BMP2(CaP Bound)

In this example the linked $Ca_2(HPO_4)_2$/hydroxyapatite BMP-2 from Example 11 (monolithic structure) hereinabove, was mechanically broken down into smaller particles (alternatively the morsels from Example 10, hereinabove, may be used resulting in a linked vancomycin containing final material). These particles were then mixed with calcium aluminate morsels (of an appropriate size distribution) to give an overall particle size distribution of no greater than 10 percent (wt)+8 mesh and the remainder being between −8 mesh and −325 mesh. This could then be cast with water addition (in the amount ranging from 5 to 50 percent by weight) into a new monolithic shape resulting from the blending and mixing of the CA and CaP resulting in a functionalized CaP containing the linked (attached) BMP-2 or vancomycin. The resulting functionalized composition has the characteristic of a plastic consistency such that the functionalized composition is mechanically pliable by the use of the human hand and adheres to natural bone where it sets (becomes hardened in place) providing mechanical support and bonding of the encompassed bone.

Example 13

CA+CaP+Collagen+BMP2(Both)

In this example, the CA is treated as described in Examples 7.1 to 7.6, hereinabove. The functionalized CA the morsels of material (i.e. modified with the linker groups) were placed in a solution of 10 ug/ml of BMP-2 and left for 24 hours at 30 degrees Centigrade. After this step, the material was dried under vacuum. This material was then blended with material from Example 11, hereinabove, which was mechanically broken down to smaller particle sizes. The resulting materials were then blended with collagen (amount ranging from greater than zero to 10 percent by weight) from one of the following sources: from bovine achilles tendon, Sigma-Aldrich-C9879, from rat tail, Sigma-Aldrich-C7661, from hydrolyzed bovine, Pure Bulk, Inc.—CLGHY00500, to give a plastic consistency. The plastic consistency was similar to the physical characteristics of a putty like material which is agglomerated and adheres together but has the characteristics of being pliable and flexible allowing for the material to be formed into any three dimensional shape or structure or allowing it to encompass or envelope other structures by being "pressed" or formed around, between, and/or into said structures when mixed with water (preferably in the amount from 1 to 50 percent by weight, and more preferably from 5 to 50 weight percent). This material was then hand formed into a three dimensional structure and allowed to set at ambient (laboratory room) temperature resulting in a hard monolith within one hour. The BMP-2 successfully attached to the functionalized CA and to the functionalized CaP. The collagen addition aids in achieving a plastic consistency of the resulting functionalized composition (material) before it is allowed to set (harden in place). The resulting functionalized composition has the characteristic of a plastic consistency such that the functionalized composition is mechanically pliable by the use of the human hand and adheres to natural bone where it sets (becomes hardened in place) within an hour providing mechanical support and bonding of the encompassed bone.

Example 14

CA+CaP+Collagen+BMP2

In this example, the hydroxyapatite composition was created from $Ca_2(HPO_4)$ according to the literature known by those skilled in the art. The resulting material was then broken down to smaller particles and blended with unmodified calcium aluminate morsels. Together, these morsels were treated according to Example 7.5, hereinabove, and then placed in a solution of 10 ug/ml BMP-2 for 24 hours, after which, the morsels were dried under vacuum. These morsels were then mixed with collagen (from greater than zero to 10 percent by weight) to give a plastic consistency when mixed with water (ranging from 5 to 50 percent by weight). This functionalized composition (material) having a plastic consistency was then hand formed into a three dimensional structure and allowed to set (harden in place) at ambient (laboratory room) temperature resulting in a hard monolith after two hours. The BMP-2 attached successfully to the functionalized CA and to the functionalized CaP. The functionalized composition in its plastic physical state was also hand formed and molded completely around a natural bone (i.e. the functionalized composition encompassed the entire natural bone structure). The functionalized composition having its plastic physical property enveloped and adhered to the entire bone structure where it was allowed to set (harden) in place at ambient (room) temperature with two hours.

Example 15

CA+Collagen+Vancomycin

In this example, a 50:50 blend of modified CA (obtained as prescribed in Examples 7.6 and 7.7, hereinabove) and unmodified CA was prepared. This 50:50 CA blend was then blended with collagen (in the amount ranging from greater than zero to 10 percent by weight) to give a plastic consistency when mixed with water (in the amount ranging from 5 to 50 percent by weight). This material was then hand formed into a three dimensional structure and allowed to set (harden) at ambient (laboratory room) temperature resulting in a hard monolith after two hours. The vancomycin successfully attached to the functionalized (modified) CA. The modified CA is either (i) fifty weight percent of a $CaAl_2O_4$ and fifty weight percent of a $CaAl_4O_7$, or (ii) ninety nine weight percent of a blend of equal parts by weight of a $CaAl_2O_4$ and a $CaAl_4O_7$ and one weight percent of a $C_{12}A_7$. The resulting functionalized composition has the characteristic of a plastic consistency such that the functionalized composition is mechanically pliable by the use of the human hand and adheres to natural bone where it sets (becomes hardened in place) providing mechanical support and bonding of the encompassed bone.

Example 16

CA+CaP+Collagen+BMP-2+Vancomycin

In this example, CA modified with vancomycin via the procedures of Example 7.6 and Example 7.7 hereinabove, was blended with CaP modified with BMP-2 via the procedures of Example 14, hereinabove, to result in a functionalized composition having CA modified with vancomycin and a CaP modified with BMP-2. Next, this functionalized composition was then blended with collagen (in the amount ranging from greater than zero to 10 percent by weight) to give a plastic consistency when mixed with water (ranging from 5 to 50 percent by weight). Next, unmodified CA (i.e. non-functionalized CA) was added to increase the rate of the 'set' so as to result in a putty like material that can be formed by hand or otherwise into complex three dimensional structures which will set at ambient (laboratory room) temperature within 1 hour resulting in a hard monolith containing modified scaffold materials (i.e. a hard functionalized body or prosthesis). The resulting material contained CA with attached vancomycin and CaP with attached BMP-2. The resulting functionalized composition has the characteristic of a plastic consistency such that the functionalized composition is mechanically pliable by the use of the human hand and adheres to natural bone where it sets (becomes hardened in place) providing mechanical support and bonding of the encompassed bone.

It will be appreciated by those persons skilled in the art that the linker groups disclosed herein employed to functionalize the calcium phosphate containing phases and optionally the calcium aluminate containing phases of the compositions of the present invention bind well to the calcium phosphate and calcium aluminate containing compositions. Those persons skilled in the art shall understand that the present applicants have shown that the calcium phosphate and calcium aluminate containing compositions of this invention may be functionalized with various head and tail groups on long alkyl chains in order to provide for further chemical or biological modification of the functionalized compositions. The present applicants have successfully functionalized such compositions, as described herein, with proteins, antibiotics, and peptide molecules.

Whereas particular embodiments of this invention have been described above for purposes of illustration, it will be evident to those persons skilled in the art that numerous variations of the details of the present invention may be made without departing from the invention as defined herein and in the appended claims.

What is claimed is:

1. A functionalized composition consisting of: at least one nonirradiated resorbable heat treated calcium phosphate non-metal substrate in the form of a monolith that is functionalized either on the surface of said calcium phosphate non-metal substrate or within an interface of at least one pore of a porous resorbable scaffold of said calcium phosphate non-metal substrate with a bidentate bond of C—O or P—O to said calcium phosphate non-metal substrate with a carbon chain, and one or more of another chemical moiety and/or one or more of a biologically active moiety, wherein said bidentate bond anchors said another chemical moiety or said biologically active moiety to said surface providing reactive locations for the attachment of either of said another chemical moiety or said biologically active moiety, or both, to said calcium phosphate non-metal substrate, wherein said functionalized calcium phosphate non-metal substrate has a surface area and modulus of rupture of cancellous bone, and wherein said functionalized calcium phosphate has a plastic consistency, wherein said porous resorbable scaffold has a macro-porosity to achieve vascularity, and wherein the hardness of said calcium phosphate non-metal substrate and natural bone are equal and abrasion is reduced, and wherein said functionalized composition is non-toxic and resists infection.

2. The functionalized composition of claim 1 wherein said biologically active moiety is at least one selected from the group of a protein, a peptide, and an antibiotic.

3. The functionalized composition of claim 2 wherein said protein is one or more selected from the group consisting of a collagen, and a transforming growth factor beta superfamily.

4. The functionalized composition of claim 3 wherein said transforming growth factor beta superfamily protein is one or more of a protein selected from the group consisting of a bone morphogenetic protein and an activin.

5. The functionalized composition of claim 4 wherein said bone morphogenetic protein is one selected from the group consisting of a BMP-2, a BMP-2/BMP-7 heterodimer, a BMP-2/BMP-4, a BMP-2a, a BMP-3, a BMP-3b/GDF-10, a BMP-4, a BMP-4/BMP-7 heterodimer, a BMP-5, a BMP-6, a BMP-7, a BMP-8, a BMP-8a, a BMP-9, a BMP-10, a BMP-15/GDF-9B, a BMP-8b, and a decapentaplegic/DPP, and combinations thereof.

6. The functionalized composition of claim 2 wherein said antibiotic is one or more selected from the group consisting of an ampicillin, a vancomycin, a penicillin, an amoxicillin, a gentamycin, and combinations thereof.

7. The functionalized composition of claim 2 wherein said peptide is a RGDC peptide (arginine-glycine-aspartate-cystein), a KRSR peptide (lysine-arginine-serine-arginine), a KRSRC peptide (lysine-arginine-serine-arginine-cysteine), or is any cysteine peptide.

8. The functionalized composition of claim 1 wherein said calcium phosphate non-metal substrate is selected from the group consisting of a calcium orthophosphate, a calcium metaphosphate, a calcium pyrophosphate, a hydroxyapatite, and combinations thereof.

9. The functionalized composition of claim 8 wherein said calcium orthophosphate is selected from the group consisting of a monocalcium phosphate, a dicalcium phosphate, a tricalcium phosphate, and combinations thereof.

10. The functionalized composition of claim 2 wherein said calcium phosphate is a tricalcium orthophosphate and said antibiotic is a vancomycin, gentamycin, or an ampicillin.

11. The functionalized composition of claim 2 wherein said calcium phosphate is a dicalcium orthophosphate and said protein is a bone morphogenetic protein-2.

12. The functionalized composition of claim 1 wherein the plastic consistency is such that the functionalized composition is mechanically pliable by the use of the human hand.

\* \* \* \* \*